United States Patent [19]

Hipskind et al.

[11] Patent Number: 5,891,875
[45] Date of Patent: Apr. 6, 1999

[54] MORPHOLINYL TACHYKININ RECEPTOR ANTAGONISTS

[75] Inventors: Philip A. Hipskind, New Palestine; Karen L. Lobb, Indianapolis, both of Ind.

[73] Assignee: Eli Lilly and Company, Indianapolis, Ind.

[21] Appl. No.: 859,138

[22] Filed: May 20, 1997

Related U.S. Application Data

[60] Provisional application No. 60/017,953 May 20, 1996.
[51] Int. Cl.$^6$ ........................ A61K 31/535; C07D 413/14
[52] U.S. Cl. ........................ 514/235.2; 514/903; 544/130; 544/143
[58] Field of Search ........................ 544/130; 514/235.2

[56] References Cited

U.S. PATENT DOCUMENTS 5,612,337 3/1997 Baker et al. ........................ 514/236.2

*Primary Examiner*—Robert W. Ramsuer
*Attorney, Agent, or Firm*—Paul J. Gaylo

[57] ABSTRACT

This invention provides methods of treating a physiological disorder associated with an excess of tachykinins in a mammal which comprises administering to a mammal in need of said treatment a compound selected from a series of substituted morpholines. This invention also provides a series of novel substituted morpholines as well as pharmaceutical formulations employing these substituted morpholines.

3 Claims, No Drawings

MORPHOLINYL TACHYKININ RECEPTOR ANTAGONISTS

PRIORITY CLAIM

This application claims the benefit of U.S. Provisional Patent Application No. 60/017,953, filed May 20, 1996.

BACKGROUND OF THE INVENTION

Since the discovery of serotonin (5-hydroxytryptamine, 5-HT) over four decades ago, the cumulative results of many diverse studies have indicated that serotonin plays a significant role in the functioning of the mammalian body, both in the central nervous system and in peripheral systems as well. Morphological studies of the central nervous system have shown that serotonergic neurons, which originate in the brain stem, form a very diffuse system that projects to most areas of the brain and spinal cord. R. A. O'Brien, *Serotonin in Mental Abnormalities*, 1:41 (1978); H. W. M. Steinbusch, HANDBOOK OF CHEMICAL NEUROANATOMY, Volume 3, Part II, 68 (1984); N. E. Anden, et al., *Acta Physiologica Scandinavia*, 67:313 (1966). These studies have been complemented by biochemical evidence that indicates large concentrations of 5-HT exist in the brain and spinal cord. H. W. M. Steinbusch, supra.

With such a diffuse system, it is not surprising that 5-HT has been implicated as being involved in the expression of a number of behaviors, physiological responses, and diseases which originate in the central nervous system. These include such diverse areas as sleeping, eating, perceiving pain, controlling body temperature, controlling blood pressure, depression, schizophrenia, and other bodily states. R. W. Fuller, BIOLOGY OF SEROTONERGIC TRANSMISSION, 221 (1982); D. J. Boullin, SEROTONIN IN MENTAL ABNORMALITIES 1:316 (1978); J. Barchas, et al., *Serotonin and Behavior*, (1973).

Serotonin plays an important role in peripheral systems as well. For example, approximately 90% of the body's serotonin is synthesized in the gastrointestinal system, and serotonin has been found to mediate a variety of contractile, secretory, and electrophysiologic effects in this system. Serotonin may be taken up by the platelets and, upon platelet aggregation, be released such that the cardiovascular system provides another example of a peripheral network that is very sensitive to serotonin. Given the broad distribution of serotonin within the body, it is understandable that tremendous interest in drugs that affect serotonergic systems exists. In particular, receptor-specific agonists and antagonists are of interest for the treatment of a wide range of disorders, including anxiety, depression, hypertension, migraine, compulsive disorders, schizophrenia, autism, neurodegenerative disorders, such as Alzheimer's disease, Parkinsonism, and Huntington's chorea, and cancer chemotherapy-induced vomiting. M. D. Gershon, et al., THE PERIPHERAL ACTIONS OF 5-HYDROXYTRYPTAMINE, 246 (1989); P. R. Saxena, et al., *Journal of Cardiovascular Pharmacology*, 15:Supplement 7 (1990).

Serotonin produces its effects on cellular physiology by binding to specialized receptors on the cell surface. It is now recognized that multiple types of receptors exist for many neurotransmitters and hormones, including serotonin. The existence of multiple, structurally distinct serotonin receptors has provided the possibility that subtype-selective pharmacological agents can be produced. The development of such compounds could result in new and increasingly selective therapeutic agents with fewer side effects, since activation of individual receptor subtypes may function to affect specific actions of the different parts of the central and/or peripheral serotonergic systems.

An example of such specificity can be demonstrated by using the vascular system as an example. In certain blood vessels, stimulation of $5\text{-HT}_1$-like receptors on the endothelial cells produces vasodilation while stimulation of $5\text{-HT}_2$ receptors on the smooth muscle cells produces vasoconstriction.

Currently, the major classes of serotonin receptors ($5\text{-HT}_1$, $5\text{-HT}_2$, $5\text{-HT}_3$, $5\text{-HT}_4$, $5\text{-HT}_5$, $5\text{-HT}_6$, and $5\text{-HT}_7$) contain some fourteen to eighteen separate receptors that have been formally classified based on their pharmacological or structural differences. [For an excellent review of the pharmacological effects and clinical implications of the various 5-HT receptor types, see Glennon, et al., *Neuroscience and Behavioral Reviews*, 14:35 (1990).]

Tachykinins are a family of peptides which share a common amidated carboxy terminal sequence. Substance P was the first peptide of this family to be isolated, although its purification and the determination of its primary sequence did not occur until the early 1970's.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3):237–243 (1985) for a review of these discoveries.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

Tachykinins play a major role in mediating the sensation and transmission of pain or nociception, especially migraine headaches, see, e.g., S. L. Shepheard, et al., *British Journal of Pharmacology*, 108:11–20 (1993); S. M. Moussaoui, et al., *European Journal of Pharmacology*, 238:421–424 (1993); and W. S. Lee, et al., *British Journal of Pharmacology*, 112:920–924 (1994).

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in U.S. Pat. No. 5,491,140, issued Feb. 13, 1996; U.S. Pat. No. 5,328,927, issued Jul. 12, 1994; U.S. Pat. No. 5,360,820, issued Nov. 1, 1994; U.S. Pat. No. 5,344,830, issued Sep. 6, 1994; U.S. Pat. No. 5,331,089, issued Jul. 19, 1994; European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; Patent Cooperation Treaty publication WO 93/011609, published Jan. 21, 1993; Canadian Patent Application 2154116, published Jan. 23, 1996; European Patent Publication 693,489, published Jan. 24, 1996; and Canadian Patent Application 2151116, published Dec. 11, 1995.

Patent Cooperation Treaty Patent Publication WO 96/11000, published Apr. 18, 1996 and European Patent Publication EP 705,600, published Apr. 10, 1996, describe a synergistic effect on the combination of a serotonin agonist and a tachykinin receptor antagonist in treating migraine. U.S. patent application Ser. No. 08/387,056, filed Feb. 10, 1995, now abandoned, describes a synergistic effect on the combination of a serotonin agonist and a tachykinin receptor antagonist in treating a variety of psychiatric disorders. U.S. patent application Ser. No. 08/408,238, filed Mar. 22, 1995, now abandoned, describes a synergistic effect on the combination of a serotonin agonist and a tachykinin receptor antagonist in treating a variety of types of pain and nociception. U.S. patent application Ser. No. 60/000074, filed Jun. 8, 1995, describes a synergistic effect on the combination of a serotonin agonist and a tachykinin receptor antagonist in treating the common cold or allergic rhinitis.

European Patent Application 0 577 394, published Jan. 5, 1994, teaches a series of morpholinyl and thiomorpholinyl tachykinin receptor antagonists. Patent Cooperation Treaty Patent Application WO 95/18124, published Jul. 6, 1995, teaches another series of substituted morpholines for use as tachykinin receptor antagonists. None of these references, nor any combination of them, teach the tachykinin receptor antagonists of the present invention.

In essence, this invention provides a class of potent non-peptidyl tachykinin receptor antagonists. By virtue of their non-peptide nature, the compounds of the present invention do not suffer from the shortcomings, in terms of metabolic instability, of known peptide-based tachykinin receptor antagonists.

SUMMARY OF THE INVENTION

This invention encompasses the compounds of Formula I

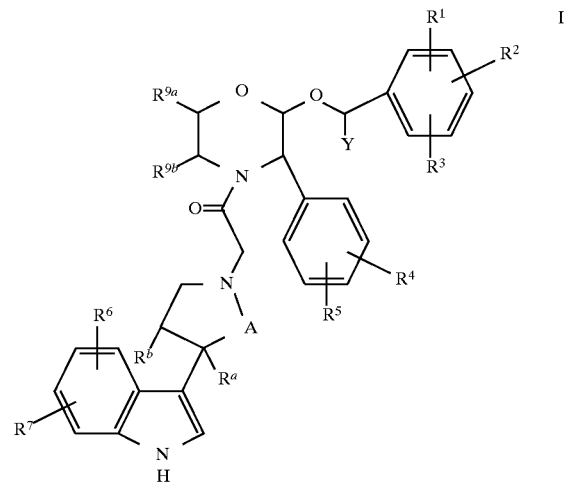

wherein:
$R^1$ is hydrogen, halo, $C_1$–$C_6$ alkyl, $C_1$–$C_6$ alkoxy, trifluoromethyl, nitro, cyano, thiol, $C_1$–$C_6$ alkylthio, $C_1$–$C_6$ alkylsulfinyl, $C_1$–$C_6$ alkylsulfonyl, $C_2$–$C_6$ alkoxycarbonyl, $C_2$–$C_6$ carbamoyl, —C(O)-di($C_1$–$C_6$ alkyl)amino, $C_2$–$C_6$ alkenyl, $C_2$–$C_6$ alkynyl, $C_2$–$C_6$ alkanoyl, or $C_1$–$C_6$ alkoxy optionally substituted with $C_1$–$C_6$ alkoxy;

$R^2$ is hydrogen, halo, $C_1$–$C_6$ alkyl, $C_1$–$C_6$ alkoxy optionally substituted with $C_1$–$C_6$ alkoxy, or trifluoromethyl;

$R^3$ is hydrogen, halo, or trifluoromethyl;

$R^4$ is hydrogen, halo, trifuoromethyl, $C_1$–$C_6$ alkyl, $C_1$–$C_6$ alkoxy, nitro, cyano, thiol, $C_1$–$C_6$ alkylthio, $C_1$–$C_6$ alkylsulfinyl, $C_1$–$C_6$ alkylsulfonyl, $C_2$–$C_6$ alkoxycarbonyl, $C_2$–$C_6$ carbamoyl, —C(O)-di($C_1$–$C_6$ alkyl)amino, $C_2$–$C_6$ alkenyl, $C_2$–$C_6$ alkynyl, $C_2$–$C_6$ alkanoyl, or $C_1$–$C_6$ alkoxy optionally substituted with $C_1$–$C_6$ alkoxy;

$R^5$ is hydrogen, halo, $C_1$–$C_6$ alkoxy optionally substituted with $C_1$–$C_6$ alkoxy, or trifluoromethyl;

$R^{9a}$ and $R^{9b}$ are each independently hydrogen, or $C_1$–$C_6$ alkyl, or are joined so to form, together with the carbon atoms to which they are attached, a $C_3$–$C_8$ cycloalkyl ring;

Y is hydrogen or $C_1$–$C_6$ alkyl, said $C_1$–$C_6$ alkyl group being optionally substituted with one or two hydroxy groups;

A is —CH$_2$—, —CH$_2$CH$_2$—, or —CH$_2$CH$_2$CH$_2$—;

$R^a$ is hydrogen or hydroxy, and $R^b$ is hydrogen, or $R^a$ and $R^b$ are taken together to form a bond;

$R^6$ and $R^7$ are independently taken from the group consisting of halo, trifluoromethyl, hydrogen, $C_1$–$C_6$ alkoxy, $C_1$–$C_6$ alkyl, $C_1$–$C_6$ alkylthio, $C_1$–$C_6$ alkylamino, hydroxy, cyano, $C_2$–$C_7$ alkanoyl, $C_2$–$C_7$ alkanoyloxy, benzamido, phenoxy, carboxamido, hydroxy, benzyloxy, phenyl($C_2$–$C_7$ alkanoyl)—, $C_1$–$C_6$ phenyl($C_2$–$C_7$ carbamoyl)—, said benzamido, phenoxy, benzyloxy, phenyl($C_2$–$C_7$ alkanoyl)—, and phenyl($C_2$–$C_7$ carbamoyl)— being optionally substituted with one or more groups selected from the group consisting of halo, trifluoromethyl, $C_1-C_6$ alkyl, $C_1-C_6$ alkoxy, cyano, hydroxy, amino and nitro;

or a pharmaceutically acceptable salt, solvate, or prodrug thereof.

This invention also provides methods of treating conditions associated with an excess of tachykinins, which comprises administering to a mammal in need thereof an effective amount of a compound of Formula I.

The present invention, in another embodiment, provides methods of treating conditions associated with an inappropriate stimulation of a serotonin receptor, which comprises administering to a mammal in need thereof, a compound of Formula I.

This invention also provides methods for treating or preventing a number of disorders characterized by their being affected, in a synergistic manner, by a combination of a serotonin agonist and a tachykinin receptor antagonist, which comprise administering to a mammal in need thereof an effective amount of a compound of Formula I or a pharmaceutically acceptable salt or solvate thereof. Among these disorders are: pain or nociception; migraine; the common cold; allergic rhinitis; or a psychiatric disorder selected from the group consisting of panic disorder, panic attack, depression, anxiety, bulimia nervosa, obsessive-compulsive disorder, premenstrual dysphoric disorder, substance abuse, substance dependence, agoraphobia, post-traumatic stress disorder, dementia of Alzheimer's type, social phobia, attention deficit hyperactivity disorder, disruptive behavior disorder, intermittent explosive disorder, borderline personality disorder, chronic fatigue syndrome, premature ejaculation, and depression and behavioral problems associated with head injury, mental retardation, and stroke.

This invention also provides pharmaceutical formulations which comprise a compound of Formula I, or a pharmaceutically acceptable salt or solvate thereof, in combination with one or more pharmaceutically acceptable carriers, diluents, or excipients therefor.

DETAILED DESCRIPTION AND PREFERRED EMBODIMENTS

The terms and abbreviations used in the instant examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "$C_1-C_6$ alkyl" refers to a straight or branched, monovalent, saturated aliphatic chain of 1 to 6 carbon atoms and includes, but is not limited to, methyl, ethyl, propyl, isopropyl, butyl, isobutyl, t-butyl, pentyl, isopentyl, and hexyl. Similarly, the term "$C_1-C_6$ alkyl" refers to a straight or branched, monovalent, saturated aliphatic chain of 4 to 7 carbon atoms.

"Halo" represents chloro, fluoro, bromo or iodo.

"$C_1-C_6$ alkoxy" represents a straight or branched alkyl chain having from one to six carbon atoms attached to an oxygen atom. Typical $C_1-C_6$ alkoxy groups include methoxy, ethoxy, propoxy, isopropoxy, butoxy, t-butoxy, pentoxy and the like.

The term "di($C_1-C_6$ alkyl)amino" refers to a compound of the formula $-NR^xR^y$ wherein $R^x$ and $R^y$ are independently a $C_1-C_6$ alkyl group. Typical di($C_1-C_6$ alkyl)amino groups include dimethylamino, methylethylamino, diisopropylamino, ethylisopropylamino, and the like.

The term "$C_2-C_7$ carbamoyl" as used herein refers to a moiety having one of the following two structures.

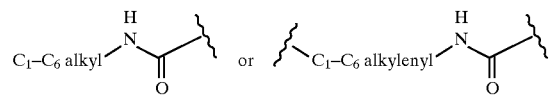

The term "$C_2-C_7$ alkanoyl" as used herein refers to a group containing one to six carbon atoms connected through a carbonyl group. Typical such groups include acetyl, propanoyl, butanoyl, and the like.

The term "$C_3-C_8$ cycloalkyl" refers to a moiety having from three to eight carbon atoms and includes cyclopropyl, cyclobutyl, cyclopentyl, and cyclooctyl.

The term "haloformate" as used herein refers to an ester of a haloformic acid, this compound having the formula

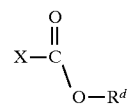

wherein X is halo, and $R^d$ is $C_1-C_6$ alkyl. Preferred haloformates are bromoformates and chloroformates. Especially preferred are chloroformates. Those haloformates wherein $R^d$ is $C_3-C_6$ are especially preferred. Most preferred is isobutylchloroformate.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4-C_7$ alkyl).

Although the free-base form of those compounds of Formula I which have a basic functionality may be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

The term "pharmaceutically acceptable salt" as used herein, refers to salts of the compounds of the above formula which are substantially non-toxic to living organisms. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of Formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solvates of the compounds of Formula I. Many of the Formula I compounds can combine with solvents such as water, methanol, ethanol and acetonitrile to form pharmaceutically acceptable solvates such as the corresponding hydrate, methanolate, ethanolate and acetonitrilate.

As noted supra the present invention also encompasses prodrugs of the compounds of Formula I. In general, such prodrugs will be functional derivatives of the compounds of Formula I which are readily convertible in vivo into the required compound of Formula I. Conventional procerues for the selection and preparation of suitable prodrug derivatives are described, for example, in DESIGN OF PRODRUGS, (H. Bundgaard, ed., 1985).

A prodrug may be a pharmacologically inactive derivative of a biologically active substance (the "parent drug" or "parent molecule") that requires transformation within the body in order to release the active drug and that has been improved delivery properties over the parent drug molecule. The transformation in vivo may be, for example, as the result of some metabolic process, such as chemical or enzymatic hydrolysis of a carboxylic, phosphoric, or sulfate ester, or reduction or oxidation of a susceptible functionality.

Thus, for example, certain preferred prodrugs may not be antagonists of tachykinin, particularly substance P, activity to any significant extent (or not at all). Such compounds, however, are still advantageous in treating the various described herein, especially where an injectable formulation is preferred.

The advantages of a prodrug may lie in its physical properties, such as enhanced water solubility for parenteral administration compared with the parent drug, or it may enhance absorption from the digestive tract, or it may enhance drug stability for long-term storage. Ideally, a prodrug will improve the overall efficiency of a parent drug, for example, through reduction of toxicity and unwanted effects of drugs by controlling their absorption, blood levels, metabolism, distribution, and cellular uptake.

A particularly preferred class of prodrugs of the compounds of the present invention is that wherein the hydroxy moiety of the group Y in Formula I (when Y is $C_1$–$C_6$ alkyl substituted by hydroxy) is derivatized.

The term "parent molecule", "parent compound", or "parent drug" refers to the biologically active entity that is release via enzymatic action of a metabolic or catabolic process, or via a chemical process following administration of the prodrug. The parent compound may also be the starting material for the preparation of its corresponding prodrug.

The compounds employed in the present invention are derivatives of morpholine which are named and numbered according to the RING INDEX, The American Chemical Society, as follows.

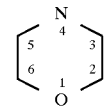

The compounds of Formula I are generally prepared by reacting a compound of Formula II

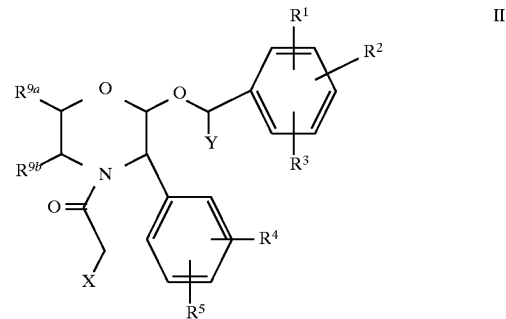

where X is a leaving group, preferably a halo group, most preferably bromo or iodo, with a compound of Formula III.

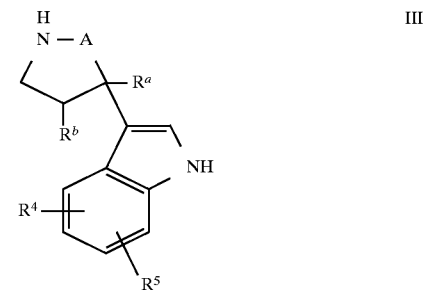

This reaction is generally performed in an organic solvent, at a temperature between −78° C. and 120° C., and the resulting product is isolated. This reaction is generally performed using equimolar amounts of the two reactants, even though other ratios may also be employed. The organic solvent used is preferably a polar aprotic solvent, for example, acetonitrile, N,N-dimethylformamide, N,N-dimethylphenylacetamide, dimethylsulfoxide, or hexamethylphosphoric triamide. Instead of using a polar aprotic solvent it is also possible to use an ether, such as tetrahydrofuran, dioxane, or methyl t-butyl ether, or a ketone, such as methyl ethyl ketone. Acetonitrile is the most preferred such solvent.

In the temperature range indicated above, the preferred temperature is 30–90° C. If acetonitrile is employed as a solvent, the reaction is advantageously carried out at the reflux point of the reaction mixture.

The product obtained in this way is isolated by the usual techniques, for example, by concentration of the solvents, followed by washing of the residue with water, and then purification by conventional techniques, such as chromatography or recrystallization.

The compounds of the present invention may also be prepared by reacting a compound of Formula IV

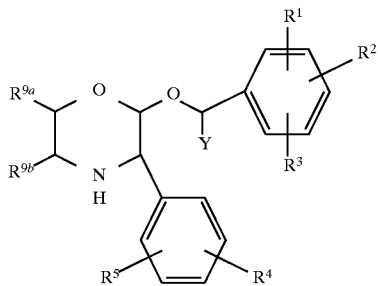

with a compound of Formula V

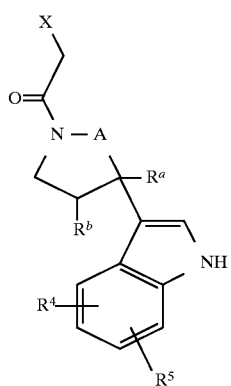

where X is a leaving group, preferably a halo group, most preferably bromo or iodo. The reaction conditions and the solvent employed for this reaction are essentially the same as for the reaction of the compounds of Formula II and III, supra.

The intermediates of Formula II are prepared essentially as described in Patent Cooperation Treaty Patent Application WO 95/18124, published Jul. 6, 1995. In general, these compounds are prepared as described in Scheme I, infra.

The following references describe methods which may be applied by the skilled worker to the chemical syntheses set forth above once the practitioner has read the disclosure herein.

(a) D. A. Evans, et al., *Journal of the American Chemical Society*, 112:4011 (1990).

(b) I. Yanagisawa, et al., *Journal of Medicinal Chemistry*, 27:849 (1984).

(c) R. Duschinsky, et al., *Journal of the American Chemical Society*, 70:657 (1948).

(d) F. N. Tebbe, et al., *Journal of the American Chemical Society*, 100:3611 (1978).

(e) N. A. Petasis, et al., *Journal of the American Chemical Society*, 112:6532 (1990).

(f) K. Takai, et al., *Journal of Organic Chemistry*, 52:4412 (1987).

Scheme I

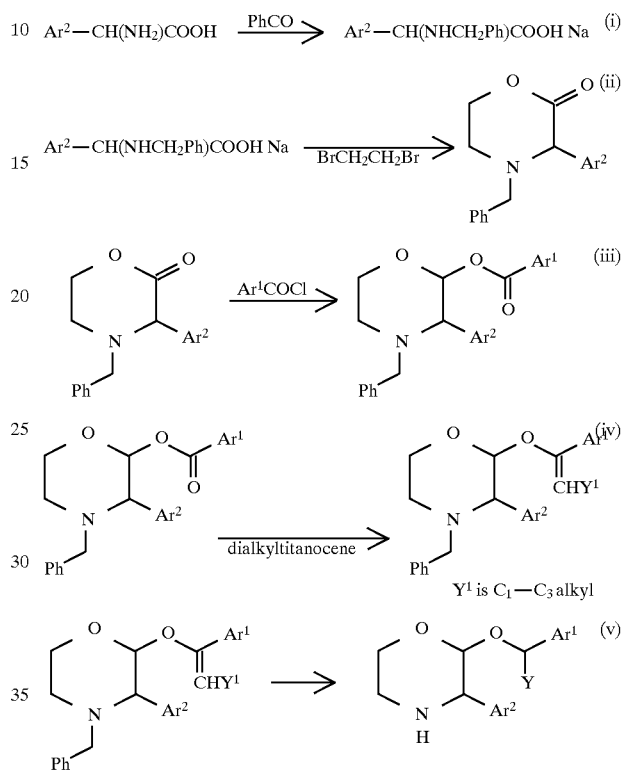

The Examples and Preparations disclosed herein produce predominantly the preferred isomers. The unfavored isomers are also produced as minor components. If desired, they may be isolated and employed to prepare the various stereoisomers in conventional manner, for example, chromatography using an appropriate column. The skilled worker will appreciate, however, that, although the Examples have been optimized to the production of the preferred isomers, variations in solvents, reagents, and the like may be employed to yield the other isomers.

PREPARATION 1

Synthesis of 4-benzyl-3-(S)-(4-fluorophenyl)-2-morpholinone

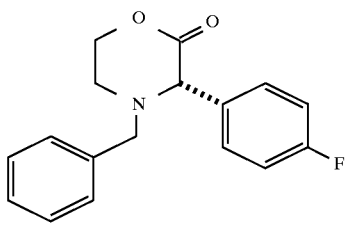

N-benzyl-(S)-(4-fluorophenyl)glycine

A solution of (S)-(4-fluorophenyl)glycine (1.87 g, 11.05 mmol) and benzaldehyde (1.12 ml, 11.1 mmol) in 11.1 ml of 1 N aqueous sodium hydroxide and 11 ml of methanol at 0° C. is treated with 165 mg (4.4 mmol) of sodium borohydride. The cooling bath is removed and the resulting mixture is stirred at room temperature for about thirty minutes. Second portions of benzaldehyde (1.12 ml, 11.1 mmol) and sodium borohydride (165 mg, 4.4 mmol) are added to the reaction mixture and stirring is continued for ninety minutes.

The reaction mixture is partitioned between 100 ml of diethyl ether and 50 ml of water and the layers are separated. The aqueous layer is separated and filtered to remove a small amount of insoluble material. The filtrate is acidified to pH 5.0 with 2 N aqueous hydrochloric acid solution and the solid that precipitated is filtered, rinsed with water, then ether, and dried to afford 1.95 grams of the title compound.

4-benzyl-3-(S)-(4-fluorophenyl)-2-morpholinone

A mixture of N-benzyl-(S)-(4-fluorophenyl)glycine (1.95 g, 7.5 mmol) N,N-diisopropylethylamine (3.90 g, 22.5 mmol), and 1,2-dibromoethane (6.50 g, 75.0 mmol) in 40 ml of N,N-dimethylformamaide is stirred at 100° C. for 20 hours. The reaction mixture is cooled and concentrated in vacuo. The residue is partitioned between 250 ml of ether and 100 ml of 0.5 N potassium hydrogen sulfate solution. The layers are separated and the organic fraction is washed with 100 ml of satureated aqueous sodium bicarbonate solution, 3×150 ml of water, and then dried over magensium sulfate. The solvents are removed in vacuo. The title product is then further purified by flash chromatography on 125 grams of silica gel using 3:1 v/v hexanes/ether as the eluant afforded 1.58 grams (74%) of the title compound as an oil.

PREPARATION 2

Synthesis of 4-benzyl-2-(R)-[3,5-bis(trifluoromethyl) benzyloxy]-3-(S)-(4-fluorophenyl)morpholine

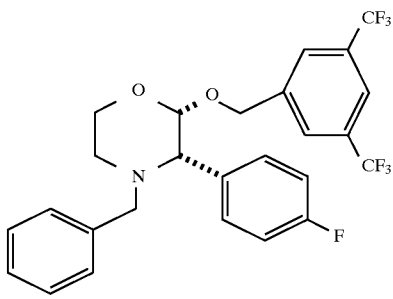

A solution of 4-benzyl-3-(S)-(4-fluorophenyl)-2-morpholinone (2.67 g, 10.0 mmol) in 40 ml of dry tetrahydrofuran is cooled to −78° C. The cold solution is treated with 12.5 ml of 1.0 M L-SELECTRIDE® (lithium tri-sec-butylborohydride) solution in tetrahydrofuran, maintaining the internal reaction temperature below −70° C. The resulting solution is stirred cold for 45 minutes and the reaction is charged with 3,5-bis(trifluoromethyl)benzoyl chloride (3.60 ml, 20.0 mmol). The resulting yellow mixture is stirred cold for 30 minutes and reaction is quenched with 50 ml of saturated aqueous sodium bicarbonate solution. The quenched reaction mixture is partitioned between 300 ml of diethyl ether and 50 ml of water. The aqueous fraction is extracted with 300 ml of diethyl ether. The organic fractions are combined and dried over magnesium sulfate. The solvents are removed in vacuo. The desired title product is then further purified by flash chromatography on 150 grams of silica gel using 37:3 v/v hexanes/diethyl ether as the eluant to afford 4.06 grams (80%) of the title product was a solid.

PREPARATION 3

Synthesis of 4-benzyl-2-(R)-[1-[3,5-bis(trifluoromethyl) phenyl]ethenyloxy]-3-(S)-(4-fluorophenyl)morpholine

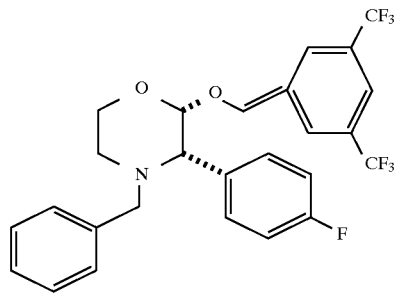

Dimethyl Titanocene

A solution of titanocene dichloride (2.49 g, 10.0 mmol) in 50 ml of diethyl ether in the dark at 0° C. is treated with 17.5 ml of 1.4 M methyllithium solution in diethylether maintaining the internal temperature below 5° C. The resulting yellow/orange mixture is stirred at toom temperature for 30 minutes and the reaction is quenched by slowly adding 25 grams of ice. The quenched reaciton mixture is diluted with 50 ml of diethyl ether and 25 ml of water and the layers are separated. The organic fraction is dried over magnesium sulfate and concentrated in vacuo to afford 2.03 grams (98%) of the title intermediate as a light-sensitive solid. The dimethyl titanocene could be stored as a solution in toluene at 0° C. for at least two weeks without apparent chemical degradation.

4-benzyl-2-(R)-[1-[3,5-bis(trifluoromethyl)phenyl] ethenyloxy]-3-(S)-(4-fluorophenyl)morpholine A solution of 4-benzyl-2-(R)-[3,5-bis(trifluoromethyl) benzyloxy]-3-(S)-(4-fluorophenyl)morpholine (2.50 g, 4.9 mmol) and dimethyl titanocene (2.50 g, 12.0 mmol) in 35 ml of a 1:1 v/v tetrahydrofuran:toluene mixture is stirred in an oil bath at 80° C. for sixteen hours. The reaction mixture is cooled and centrated in vacuo. Flash chromatography on 150 grams of silica gel using 3:1 v/v hexanes:methylene chloride as the eluant affords 1.71 grams (69%) of the title compound as a solid. If desired, an anlytical sample may be obtained by recrystallization from isopropanol.

PREPARATION 4

Synthesis of 2-(R)-[1-[3,5-bis(trifluoromethyl)phenyl] ethoxy]-3-(S)-(4-fluorophenyl)morpholine

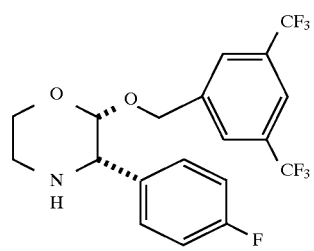

In a mixture of ethyl acetate (50 ml) and isopropanol (16 ml) 4-benzyl-2-(R)-[1-[3,5 -bis(trifluoromethyl)phenyl]

ethenyloxy]-3-(S)-(4-fluorophenyl)morpholine (4.0 g) is dissolved. To this solution 5% palladium on activated charcoal is added and the reaction mixture is hydrogenated at 40 psi for 36 hours. The catalyst is removed by filtration through CELITE™ and the solvents are removed in vacuo. The effluent is purified by flash chromatography on silica using 100% ethyl acetate and then 1–10% methanol in ethyl acetate. This affords isomer A (15%) and isomer B (80%) as clear oils, isomer B crystallized on standing.

To a solution of this free base in diethyl ether (10 ml) is added 1 M hydrochloric acid in methanol (1.75 ml total). The solution is evaporated to dryness. On the addition of diethyl ether crystals form. The solution is filtered and the residue is washed with diethyl ether to give the title compound as its hydrochloric salt.

PREPARATION 5

Synthesis of 4-benzyl-3-(S)-(4-fluorophenyl)-2-(R)-(3-fluoro-5-trifluoromethylbenzyloxy)morpholine

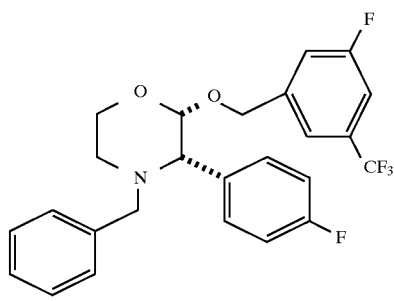

The title compound is prepared from the reaction of the compound of Preparation 1 with 3-fluoro-5-(trifluoromethyl)benzoyl chloride essentially as described in Preparation 2, supra.

PREPARATION 6

Synthesis of 4-benzyl-3-(S)-(4-fluorophenyl)-2-(R)-[1-(3-fluoro-5-trifluoromethylphenyl)ethenyloxy)morpholine

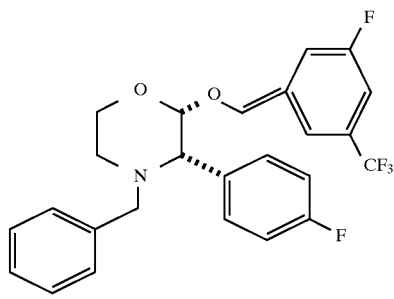

The title compound is prepared from the compound of Preparation 5 employing the procedure illustrated in Preparation 3.

PREPARATION 7

Synthesis of 3-(S)-(4-fluorophenyl)-2-(R)-[1-(3-fluoro-5-trifluoromethylphenyl)ethoxy]morpholine

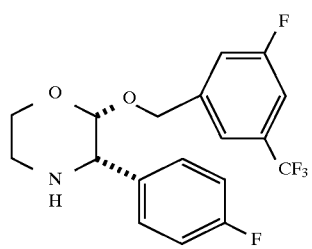

The compound of Preparation 6 is hydrogenated according to the method illustrated in Preparation 4. This affords a mixture of two epimeric products isomer A and isomer B (the major product) as clear oils.

PREPARATION 8

Preparation of 4-bromoacetyl-3-(S)-(4-fluorophenyl)-2-(R)-[1-[3,5-bis(trifluoromethyl)phenyl]ethoxy]morpholine

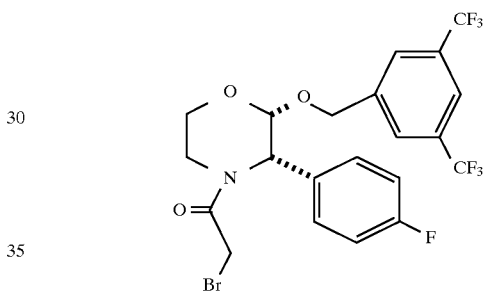

To a stirring solution of 3-(S)-(4-fluorophenyl)-2-(R)-[1-[3,5-bis(trifluoromethyl)phenyl]ethoxy]morpholine (1 eq.) and two molar equivalents of sodium carbonate in 100 ml of dry tetrahydrofuran is added bromoacetyl bromide (1 eq.). The resulting mixture is then stirred at room temperature for about one hour. The progress of the reaction is monitored by thin layer chromatography.

The reaction mixture is stirred at room temperature overnight after the addition of more bromoacetyl bromide. After the overnight stirring additional sodium carbonate (2.76 g) and bromoacetyl bromide (0.5 ml) may be added and the reaction may be stirred an additional few minutes.

The reaction mixture is then poured into 600 ml of ethyl acetate and is washed three times with water, followed by washes with dilute hydrochloric acid, water and brine. The organic fraction is dried over sodium sulfate and the solvents are removed by vacuum.

PREPARATION 9

Preparation of 4-chloroacetyl-3-(S)-(4-fluorophenyl)-2-(R)-[1-[3,5-bis(trifluoromethyl)phenyl]ethoxy]morpholine

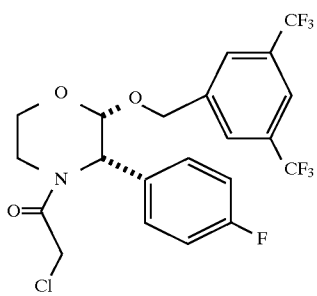

The title intermediate is prepared essentially as described in Preparation 8, supra, except that chloroacetyl chloride is employed in place of bromoacetyl bromide.

The compounds of Formulae III and V may be prepared by methods well known to one of ordinary skill in the art, including as described in U.S. Pat. Nos. 5,521,197, issued May 28, 1996, and 5,521,196, issued May 28, 1996, the entire contents of which are herein incorporated by reference. A majority of the starting indoles are commercially available, however, they may be prepared by the Fischer indole synthesis (Robinson, THE FISCHER INDOLE SYNTHESIS, Wiley, New York, 1983).

The indoles are condensed with 4-piperidone.HCl.H$_2$O in the presence of a suitable base to give the corresponding 3-(1,2,3,6-tetrahydro-4-pyridinyl)-1H-indoles as illustrated in the following scheme.

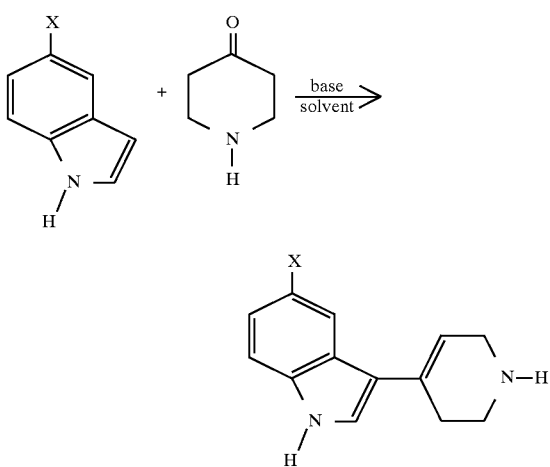

The reaction is performed by first dissolving an excess of the base, typically sodium or potassium hydroxide, in a lower alkanol, typically methanol or ethanol. The indole and two equivalents of 4-piperidone.HCl.H$_2$O are then added and the reaction refluxed for 8–72 hours. The resulting 3-(1,2,3,6-tetrahydro-4-pyridinyl)-1H-indoles may be isolated from the reaction mixture by the addition of water. Compounds which precipitate may be isolated directly by filtration while others may be extracted with a water immiscible solvent such as ethyl acetate or dichloromethane. The compounds recovered may be used directly in subsequent steps or first purified by silica gel chromatography or recrystallization from a suitable solvent.

The 3-(1,2,5,6-tetrahydro-4-pyridinyl)-1H-indoles may next be hydrogenated to give the corresponding 3-(piperidin-4-yl)-1H-indoles as shown below.

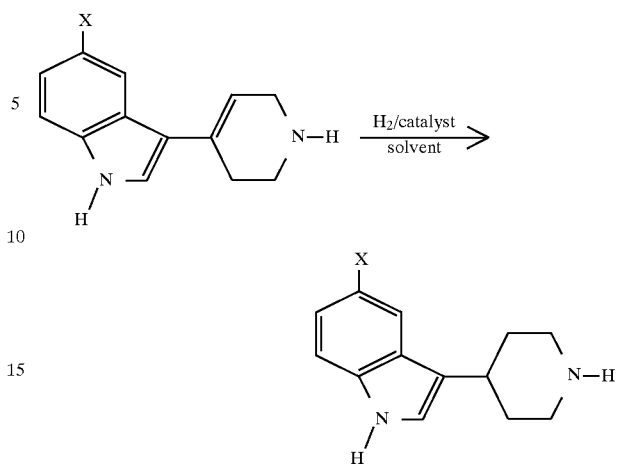

The catalyst may be a precious metal catalyst such as platinum oxide, or palladium or platinum on a suitable support such as carbon. When X is a functional group that is labile to hydrogenolysis, such as halo or benzyloxy, a deactivated catalyst such as sulfided platinum on carbon or a mixed catalyst system of sulfided platinum on carbon with platinum oxide may be used to prevent hydrogenolysis. The solvent may consist of a lower alkanol, such as methanol or ethanol, tetrahydrofuran or a mixed solvent system of tetrahydrofuran and ethyl acetate. The hydrogenation may be performed at an initial hydrogen pressure of 20–80 p.s.i., preferably from 50–60 p.s.i., at 0–60° C., preferably at ambient temperature to 40° C., for 1 hour to 3 days. Additional charges of hydrogen may be required to drive the reaction to completion depending on the specific substrate. The 3-(piperidin-4-yl)-1H-indoles prepared in this manner are isolated by removal of the catalyst by filtration followed by concentration of the reaction solvent under reduced pressure. The product recovered may be used directly in a subsequent step or further purified by chromatography or recrystallization from a suitable solvent.

All of the 3-[1,2,3,6-tetrahydro-4-pyridinyl]-1H-indoles useful as intermediates for compounds of this invention may be prepared as described in the following procedure.

PREPARATION 10

5-bromo-3-[1,2,3, 6-tetrahydro-4-pyridinyl]-1H-indole

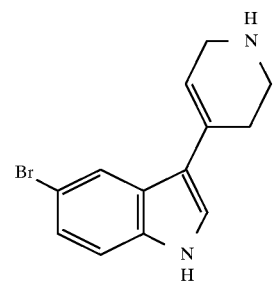

To a solution of 4.29 gm (77 mmol) potassium hydroxide in 50 ml methanol were added 5.0 gm (26 mmol) 5-bromoindole and 7.84 gm (51 mmol) 4-piperidone.HCl.H$_2$O and the reaction mixture was stirred for 18 hours at reflux under a nitrogen atmosphere. The reaction mixture was cooled to ambient temperature, diluted with 500 ml water and the mixture extracted well with dichloromethane. The combined organic extracts were washed with water followed by saturated aqueous sodium chloride and dried over sodium sulfate. The remaining organics were concentrated under reduced pressure to give 6.23 gm (86.5%) of the title compound as a yellow oil. $^1$H-NMR(DMSO-d$_6$): δ8.00 (s,1H); 7.40 (s, 1H); 7.30(d, 1H); 7.20 (d, 1H); 6.10 (s, 1H); 3.35 (br s, 2H); 2.85 (m, 2H); 2.35 (br s, 2H).

All of the 3-[piperidin-4-yl]-1H-indoles useful as intermediates for compounds of this invention may be prepared as described in the following procedure.

PREPARATION 11

5-bromo-3-[piperidin-4-yl]-1H-indole

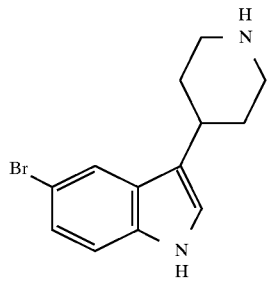

To a solution of 13.61 gm (49 mmol) 5-bromo-3-[1,2,3, 6-tetrahydro-4-pyridinyl]-1H-indole in 75 ml 2:1 tetrahydro-furan:ethyl acetate were added 8.0 gm 3% sulfided platinum on carbon and 4.0 gm platinum oxide. The reaction mixture was hydrogenated with an initial hydrogen pressure of 60 p.s.i. at 40° C. for 18 hours and then at ambient temperature for 30 hours. The reaction mixture was filtered and the filtrate concentrated under reduced pressure to give 10.33 gm (75.6%) of the title compound as a light yellow solid. MS(m/e): 278(M$^+$). $^1$H-NMR(DMSO-d$_6$): d10.6 (s,1H); 7.2 (d,1H); 7.05 (s, 2H); 6.7 (d, 1H); 3.15 (s, 1H); 3.05 (s, 1H); 2.8 (m, 3H), 1.95 (s, 1H); 1.85 (s, 1H); 1.6 (m, 2H).

PREPARATION 12

5-carboxamidoindole

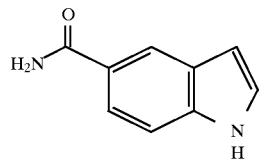

To a solution of 8.06 gm (50 mmol) indole-5-carboxylic acid in 150 ml dimethylformamide were added 8.11 gm (50 mmol) carbonyldiimidazole and the reaction mixture stirred at ambient temperature for 3 hours. The reaction mixture was then added dropwise to 150 ml concentrated ammonium hydroxide and the reaction mixture was stirred for 18 hours at ambient temperature. The reaction mixture was concentrated under reduced pressure to give a viscous oil which was subjected to silica gel chromatograpy, eluting with a gradient of dichloromethane containing 0–10% methanol. Fractions shown to contain product were combined and concentrated under reduced pressure to give the title compound as an oil which crystallizes upon standing. $^1$H-NMR (CDCl$_3$): d8.18 (s, 1H); 7.74 (d, 1H); 7.45 (d, 1H); 7.35 (s, 1H); 6.65 (s, 1H).

PREPARATION 13

5-(4-fluorobenzoyl)amino-3-(piperidin-4-yl)-1H-indole

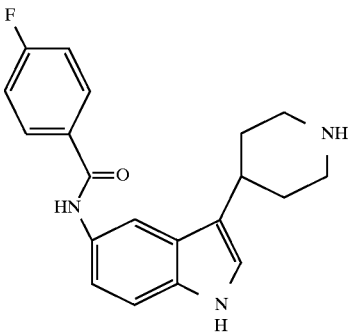

The title intermediate is prepared essentially as described in co-pending U.S. patent application Ser. No. 08/619,783, filed Mar. 20, 1996, the entire contents of which are herein incorporated by reference. To a solution of 3.93 gm (11.7 mmol) 5-(4-fluorobenzoyl)amino-3-(1,2,3,6-tetrahydropyridin-4-yl)-1H-indole in 125 ml methanol are added 0.815 gm 5% palladium on carbon. The mixture is hydrogenated at ambient temperature for 18 hours with an initial hydrogen pressure of 60 p.s.i. The reaction mixture is filtered and the filtrate concentrated under reduced pressure. The residual oil is purified by flash chromatography, eluting with 90:10 dichloromethane:methanol. Fractions shown to contain product are combined and concentrated under reduced pressure to yield the title compound as colorless crystals. m.p.=229–230° C. (methanol) MS(m/e): 337(M$^+$) Calculated for: C$_{20}$H$_{20}$N$_3$OF: Theory: C, 71.20; H, 5.98; N, 12.45. Found: C, 71.46; H, 6.17; N, 12.40.

The other compounds of Formula III may be prepared essentially as described above using commercially available starting materials. The compounds of Formula V may be prepared from the corresponding compound of Formula III by haloacetylation as described in Preparation 8. Processes for preparing these intermediates are described in U.S. Pat. Nos. 5,521,196, issued May 28, 1996, and 5,521,197, issued May 28, 1996 and co-pending U.S. patent application Ser. No. 08/619,783, filed Mar. 20, 1996, the entire contents of which are herein incorporated by reference.

The remaining compounds of Formulae II and IV may be prepared essentially as described in Patent Cooperation Treaty Patent Application WO 95/18124, published Jul. 6, 1995.

EXAMPLE 1

Preparation of 4-{[4-[5-[(benzylamino)carbonyl]indol-3-yl]-1,2,3,6-tetrahydropyridin-1-yl]acetyl}-3-(S)-(4-fluorophenyl)-2-(R)-[1-[3,5-bis(trifluoromethyl)phenyl] ethoxy]morpholine

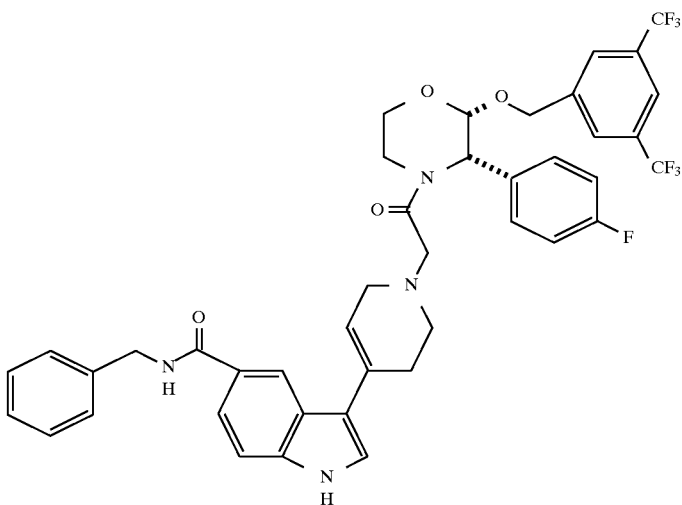

A 10 ml tear drop flask is charged with 4-bromoacetyl-3-(S)-(4-fluorophenyl)-2-(R)-[1-[3,5-bis(trifluoromethyl)phenyl]ethoxy]morpholine (1 eq.), powdered potassium carbonate (4 eq.) and 4-[5-[(benzylamino)carbonyl]indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

EXAMPLE 2

Preparation of 4-{[4-[5-(hydroxy)indol-3-yl]-1,2,3,6-tetrahydropyridin-1-yl]acetyl}-3-(S)-(4-fluorophenyl)-2-(R)-[1-[3,5-bis(trifluoromethyl)phenyl]ethoxy]morpholine

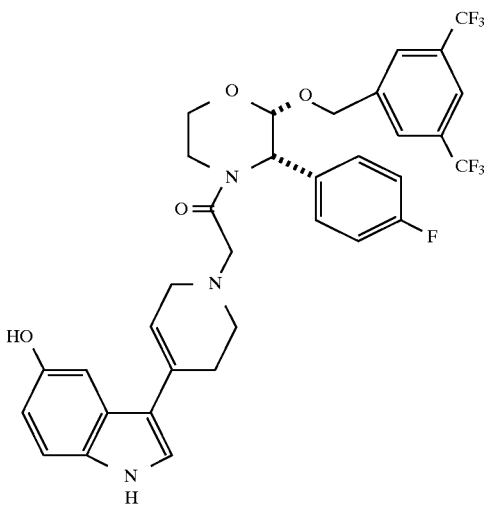

A 10 ml tear drop flask is charged with 4-bromoacetyl-3-(S)-(4-fluorophenyl)-2-(R)-[1-[3,5-bis(trifluoromethyl)phenyl]ethoxy]morpholine (1 eq.), powdered potassium carbonate (4 eq.) and 4-[5-(hydroxy)indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

EXAMPLE 3

Preparation of 4-{[4-[5-(4-fluorobenzoylamino)indol-3-yl]-1,2,3,6-tetrahydropyridin-1-yl]acetyl}-3-(S)-(4-fluorophenyl)-2-(R)-[1-[3,5-bis(trifluoromethyl)phenyl]ethoxy]morpholine

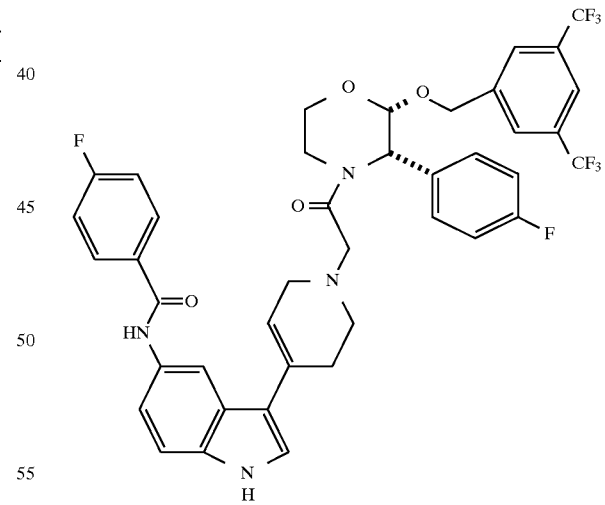

A 10 ml tear drop flask is charged with 4-bromoacetyl-3-(S)-(4-fluorophenyl)-2-(R)-[1-[3,5-bis(trifluoromethyl)phenyl]ethoxy]morpholine (1 eq.), powdered potassium carbonate (4 eq.) and 4-[5-(4-fluorobenzoylamino)indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

EXAMPLE 4

Preparation of 4-{[4-[5-(4-fluorobenzoylamino)indol-3-yl]-piperidin-1-yl]acetyl}-3-(S)-(4-fluorophenyl)-2-(R)-[1-[3,5-bis(trifluoromethyl)phenyl]ethoxy]morpholine

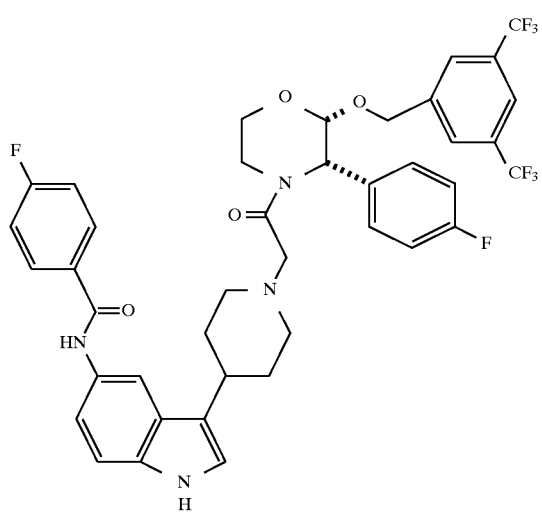

A 10 ml tear drop flask is charged with 4-bromoacetyl-3-(S)-(4-fluorophenyl)-2-(R)-[1-[3,5-bis(trifluoromethyl)phenyl]ethoxy]morpholine (1 eq.), powdered potassium carbonate (4 eq.) and 4-[5-(hydroxy)indol-3-yl]-piperidine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

The following Examples are prepared essentially as described in the above examples, except that other intermediates are employed.

EXAMPLE 5

Preparation of 4-{[4-[5-(4-trifluoromethylbenzoylamino)indol-3-yl]-piperidin-1-yl]acetyl}-3-(S)-(4-fluorophenyl)-2-(R)-[1-[3,5-bis(trifluoromethyl)phenyl]ethoxy]morpholine

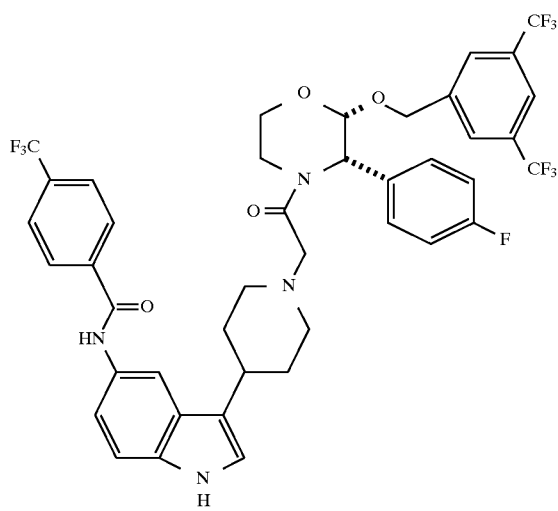

EXAMPLE 6

Preparation of 4-{[4-[5-(4-isopropylbenzoylamino)indol-3-yl]-piperidin-1-yl]acetyl}-3-(S)-(4-fluorophenyl)-2-(R)-[1-[3,5-bis(trifluoromethyl)phenyl]ethoxy]morpholine

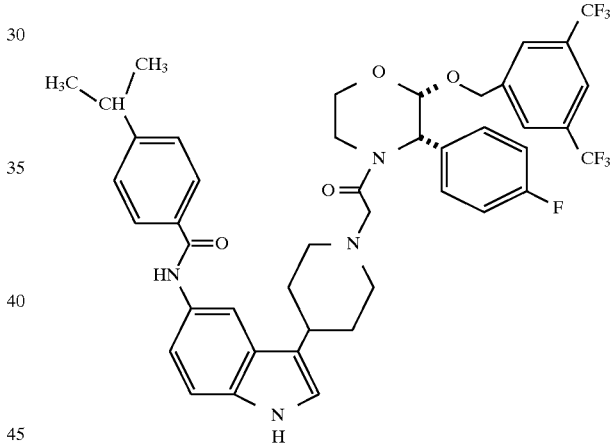

EXAMPLE 7

Preparation of 4-{[4-[5-(4-isopropylbenzoyl)indol-3-yl]-piperidin-1-yl]acetyl}-3-(S)-(4-fluorophenyl)-2-(R)-[1-[3,5-bis(trifluoromethyl)phenyl]ethoxy]morpholine

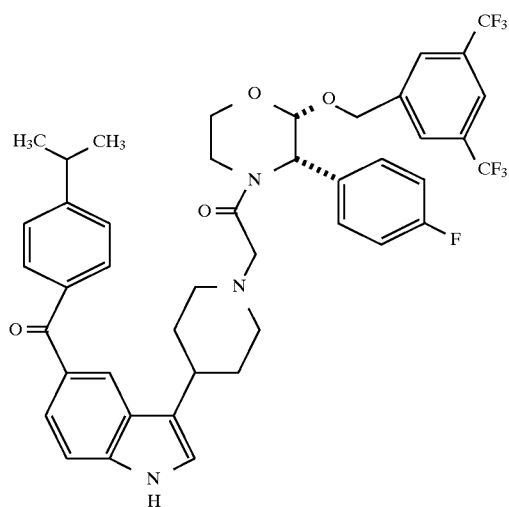

EXAMPLE 8

Preparation of 4-{[4-[5-(4-fluorobenzoyl)indol-3-yl]-piperidin-1-yl]acetyl}-3-(S)-(4-fluorophenyl)-2-(R)-[1-[3,5-bis(trifluoromethyl)phenyl]ethoxy]morpholine

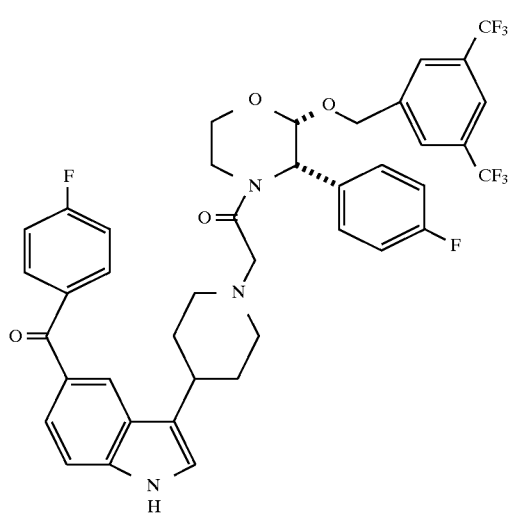

EXAMPLE 9

Preparation of 4-{[4-[5-[[(4-isopropylphenyl)amino]carbonyl]indol-3-yl]-piperidin-1-yl]acetyl}-3-(S)-(4-fluorophenyl)-2-(R)-[1-[3,5-bis(trifluoromethyl)phenyl]ethoxy]morpholine

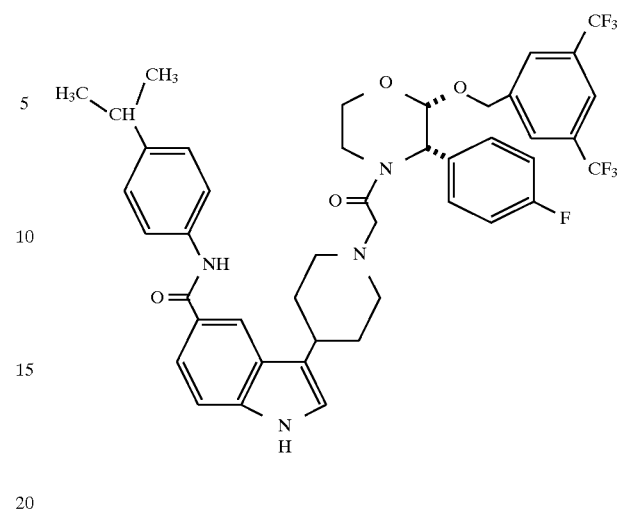

EXAMPLE 10

Preparation of 4-{[4-[5-[[(4-methoxyphenyl)amino]carbonyl]indol-3-yl]-piperidin-1-yl]acetyl}-3-(S)-(4-fluorophenyl)-2-(R)-[1-[3,5-bis(trifluoromethyl)phenyl]ethoxy]morpholine

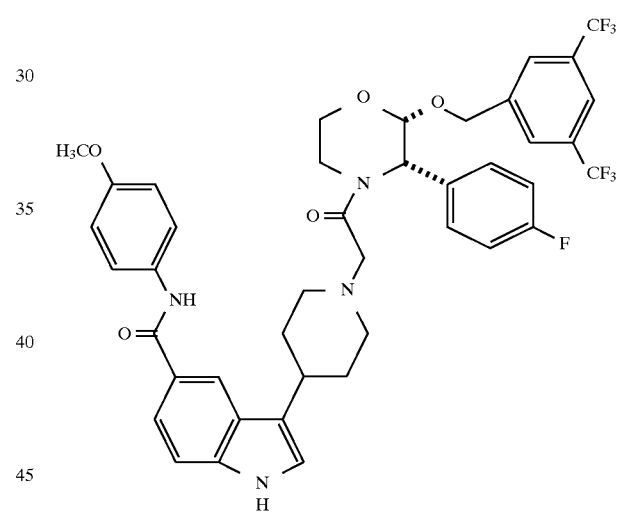

EXAMPLE 11

Preparation of 4-{[4-[5-[[(4-methoxyphenyl)amino]carbonyl]indol-3-yl]-1,2,3,6-tetrahydropyridin-1-yl]acetyl}-3-(S)-(4-fluorophenyl)-2-(R)-[1-[3,5-bis(trifluoromethyl)phenyl]ethoxy]morpholine

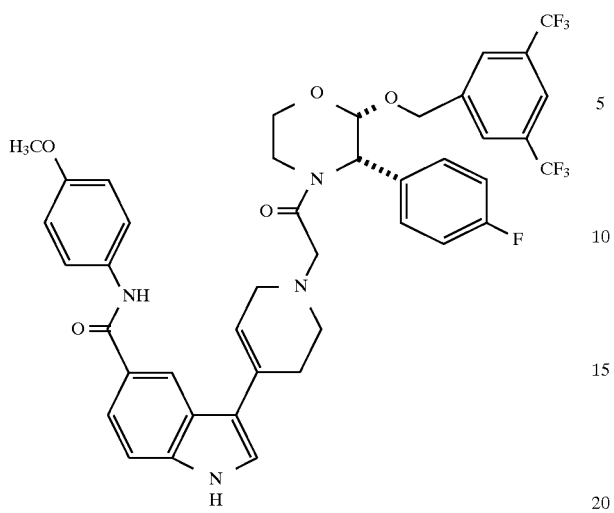

EXAMPLE 12

Preparation of 4-{[4-[5-(methoxy)indol-3-yl]-1,2,3,6-tetrahydropyridin-1-yl]acetyl}-3-(S)-(4-fluorophenyl)-2-(R)-[1-[3,5-bis(trifluoromethyl)phenyl]ethoxy]morpholine

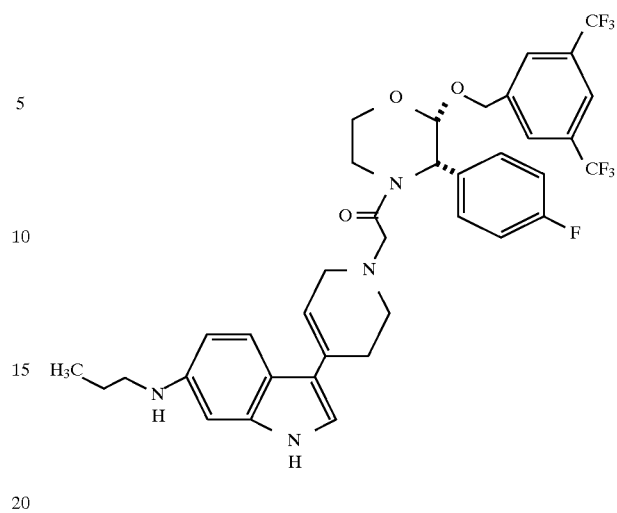

EXAMPLE 13

Preparation of 4-{[4-[6-(propylamino)indol-3-yl]-piperidin-1-yl]acetyl}-3-(S)-(4-fluorophenyl)-2-(R)-[1-[3,5-bis(trifluoromethyl)phenyl]ethoxy]morpholine

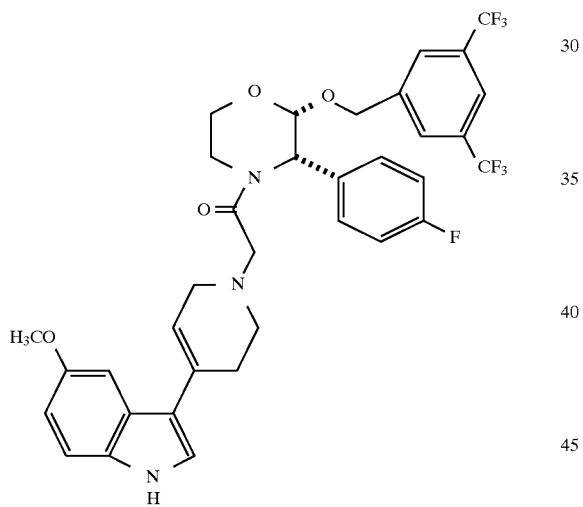

EXAMPLE 12a

Preparation of 4-{[4-[6-(propylamino)indol-3-yl]-1,2,3,6-tetrahydropyridin-1-yl]acetyl}-3-(S)-(4-fluorophenyl)-2-(R)-[1-[3,5-bis(trifluoromethyl)phenyl]ethoxy]morpholine

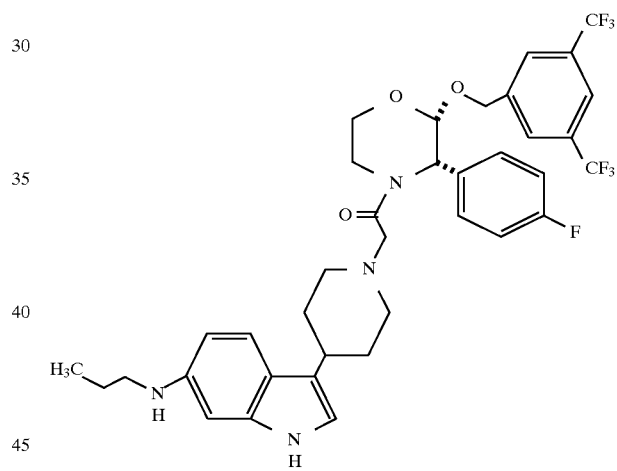

EXAMPLE 13a

Preparation of 4-{[4-[6-(acetyl)indol-3-yl]-piperidin-1-yl]acetyl}-3-(S)-(4-fluorophenyl)-2-(R)-[1-[3,5-bis(trifluoromethyl)phenyl]ethoxy]morpholine

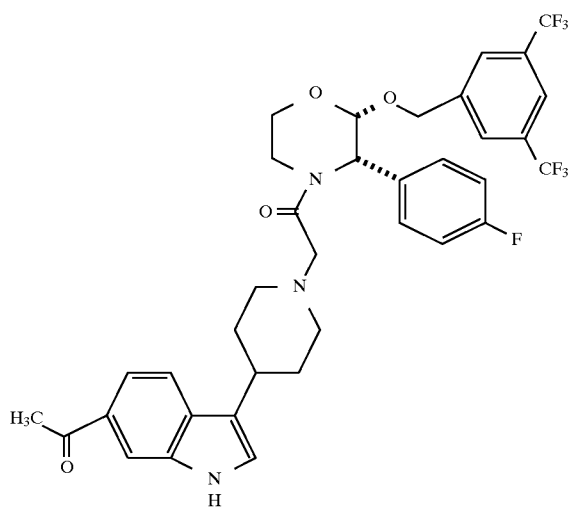

EXAMPLE 14

Preparation of 4-{[4-[5-(acetoxy)indol-3-yl]-piperidin-1-yl]acetyl}-3-(S)-(4-fluorophenyl)-2-(R)-[1-[3,5-bis(trifluoromethyl)phenyl]ethoxy]morpholine

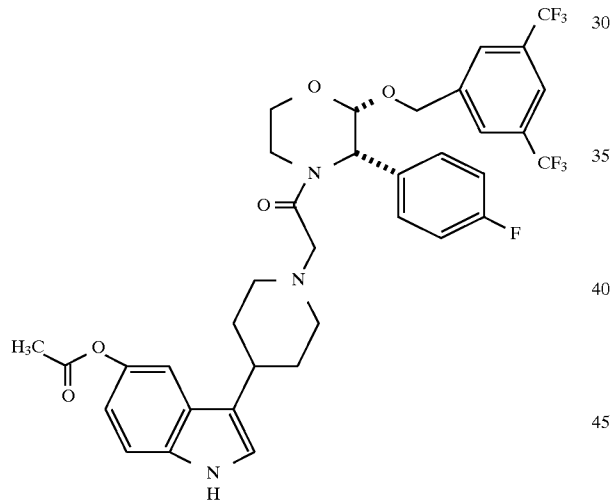

EXAMPLE 15

Preparation of 4-{[4-[5-(phenoxy)indol-3-yl]-piperidin-1-yl]acetyl}-3-(S)-(4-fluorophenyl)-2-(R)-[1-[3,5-bis(trifluoromethyl)phenyl]ethoxy]morpholine

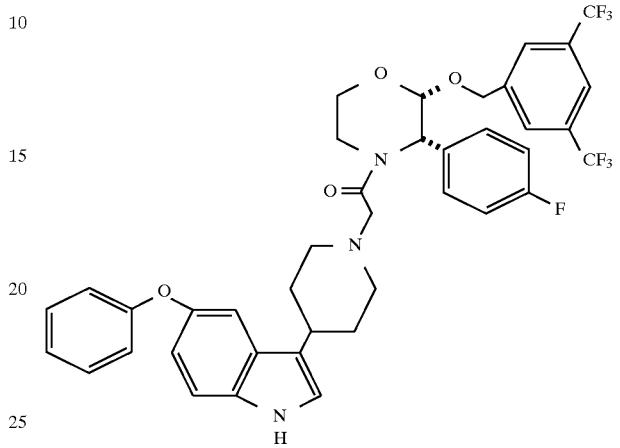

EXAMPLE 16

Preparation of 4-{[4-[5-[(benzylamino)carbonyl]indol-3-yl]-1,2,3,6-tetrahydropyridin-1-yl]acetyl}-3-(S)-(4-methylphenyl)-2-(R)-[1-[3,5-bis(trifluoromethyl)phenyl]ethoxy]morpholine

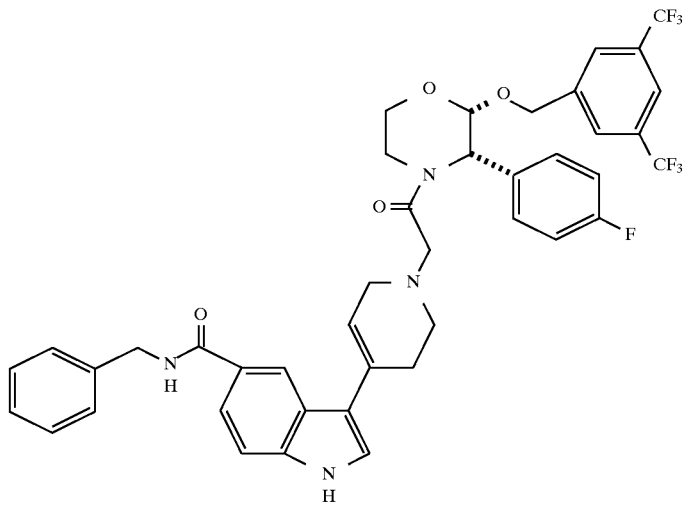

A 10 ml tear drop flask is charged with 4-bromoacetyl-3-(S)-(4-methylphenyl)-2-(R)-[1-[3,5-bis(trifluoromethyl)phenyl]ethoxy]morpholine (1 eq.), powdered potassium carbonate (4 eq.) and 4-[5-[(benzylamino)carbonyl]indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

EXAMPLE 17

Preparation of 4-{[4-[5-(hydroxy)indol-3-yl]-1,2,3,6-tetrahydropyridin-1-yl]acetyl}-3-(S)-(4-trifluoromethylphenyl)-2-(R)-[1-[3,5-bis(trifluoromethyl)phenyl]ethoxy]morpholine

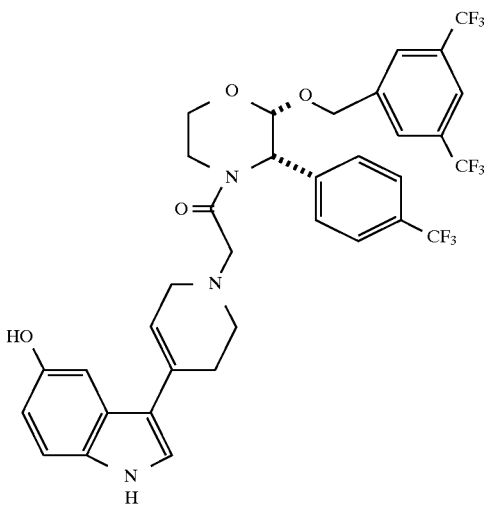

A 10 ml tear drop flask is charged with 4-bromoacetyl-3-(S)-(4-trifluoromethylphenyl)-2-(R)-[1-[3,5-bis(trifluoromethyl)phenyl]ethoxy]morphohne (1 eq.), powdered potassium carbonate (4 eq.) and 4-[5-(hydroxy)indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

EXAMPLE 18

Preparation of 4-{[4-[5-(4-fluorobenzoylamino)indol-3-yl]-1,2,3,6-tetrahydropyridin-1-yl]acetyl}-3-(S)-[4-(prop-2-enyl)phenyl]-2-(R)-[1-[3,5-bis(trifluoromethyl)phenyl]ethoxy]morpholine

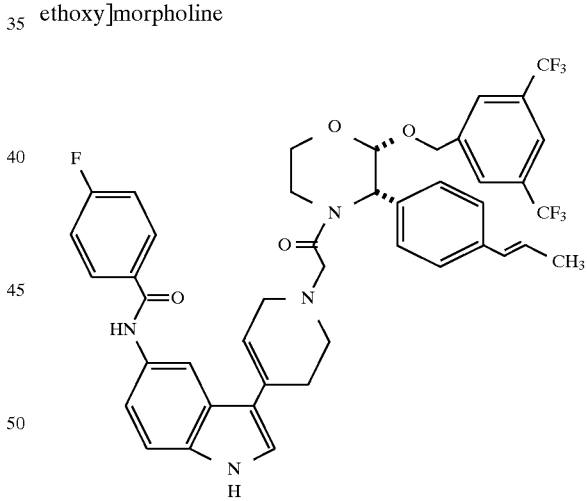

A 10 ml tear drop flask is charged with 4-bromoacetyl-3-(S)-[4-(prop-2-enyl)phenyl]-2-(R)-[1-[3,5-bis(trifluoromethyl)phenyl]ethoxy]morpholine (1 eq.), powdered potassium carbonate (4 eq.) and 4-[5-(4-fluorobenzoylamino)indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

EXAMPLE 19

Preparation of 4-{[4-[5-(4-fluorobenzoylamino)indol-3-yl]-piperidin-1-yl]acetyl}-3-(S)-(4-isopropylphenyl)-2-(R)-[1-[3,5-bis(trifluoromethyl)phenyl]ethoxy]morpholine

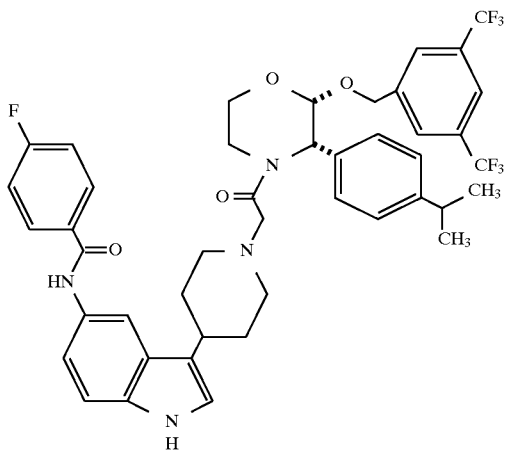

A 10 ml tear drop flask is charged with 4-bromoacetyl-3-(S)-(4-isopropylphenyl)-2-(R)-[1-[3,5-bis(trifluoromethyl)phenyl]ethoxy]morpholine (1 eq.), powdered potassium carbonate (4 eq.) and 4-[5-(hydroxy)indol-3-yl]-piperidine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

The following Examples are prepared essentially as described in the above examples, except that other intermediates are employed.

EXAMPLE 20

Preparation of 4-{[4-[5-(4-trifluoromethylbenzoylamino)indol-3-yl]-piperidin-1-yl]acetyl}-3-(S)-(4-propylsulfonylphenyl)-2-(R)-[1-[3,5-bis(trifluoromethyl)phenyl]ethoxy]morpholine

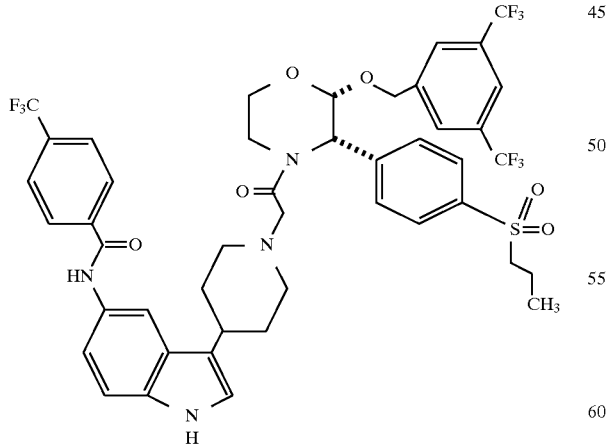

EXAMPLE 21

Preparation of 4-{[4-[5-(4-isopropylbenzoylamino)indol-3-yl]-piperidin-1-yl]acetyl}-3-(S)-(3,4-dimethoxyphenyl)-2-(R)-[1-[3,5-bis(trifluoromethyl)phenyl]ethoxy]morpholine

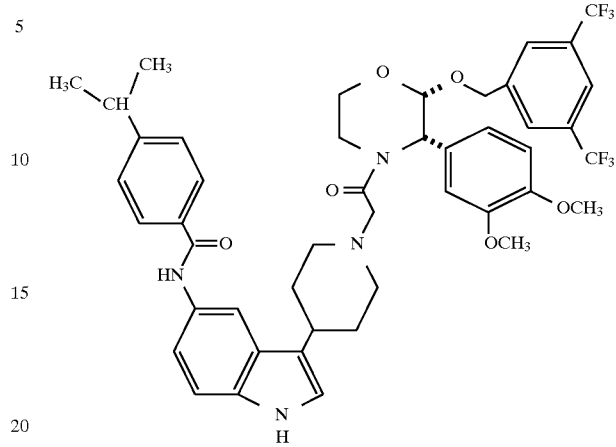

EXAMPLE 22

Preparation of 4-{[4-[5-(4-isopropylbenzoyl)indol-3-yl]-piperidin-1-yl]acetyl}-3-(S)-(3-acetylphenyl)-2-(R)-[1-[3,5-bis(trifluoromethyl)phenyl]ethoxy]morpholine

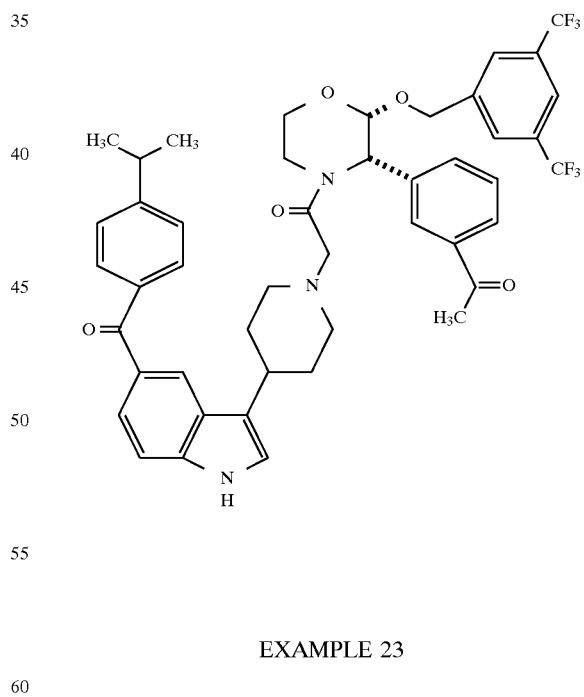

EXAMPLE 23

Preparation of 4-{[4-[5-(4-fluorobenzoyl)indol-3-yl]-piperidin-1-yl]acetyl}-3-(S)-(4-cyanophenyl)-2-(R)-[1-[3,5-bis(trifluoromethyl)phenyl]ethoxy] morpholine

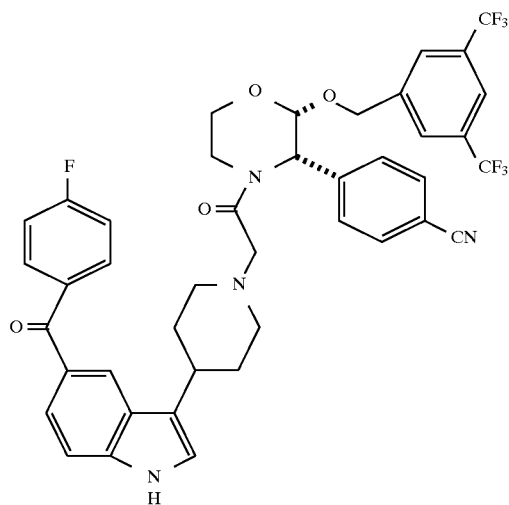

EXAMPLE 24

Preparation of 4-{[4-[5-[[(4-isopropylphenyl)amino]carbonyl]indol-3-yl]-piperidin-1-yl]acetyl}-3-(S)-{4-[(N,N,-dimethylamino)carbonyl]fluorophenyl}-2-(R)-[1-[3,5-bis(trifluoromethyl)phenyl]ethoxy]morpholine

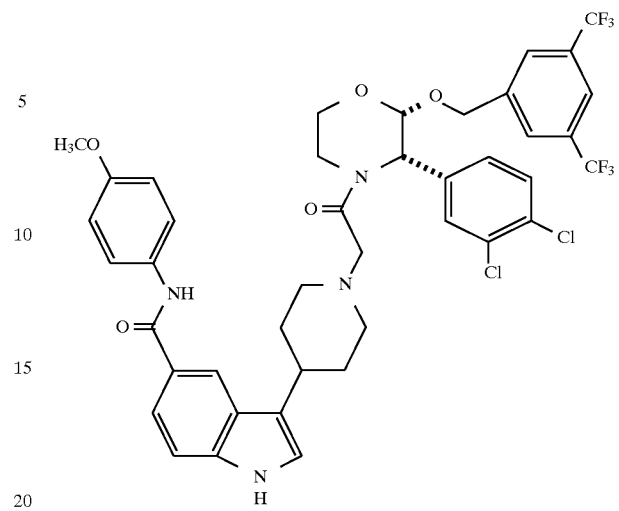

EXAMPLE 26

Preparation of 4-{[4-[5-[[(4-methoxyphenyl)amino]carbonyl]indol-3-yl]-1,2,3,6-tetrahydropyridin-1-yl]acetyl}-3-(S)-(4-methylthiophenyl)-2-(R)-[1-[3,5-bis(trifluoromethyl)phenyl]ethoxy]morpholine

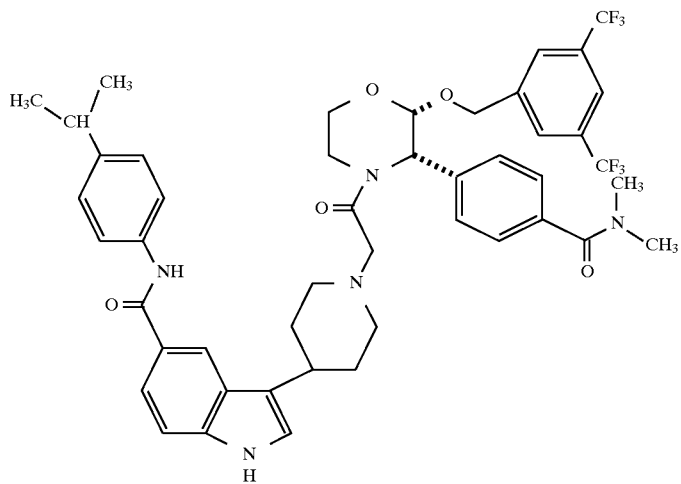

EXAMPLE 25

Preparation of 4-{[4-[5-[[(4-methoxyphenyl)amino]carbonyl]indol-3-yl]-piperidin-1-yl]acetyl}-3-(S)-(3,4-dichlorophenyl)-2-(R)-[1-[3,5-bis(trifluoromethyl)phenyl]ethoxy]morpholine

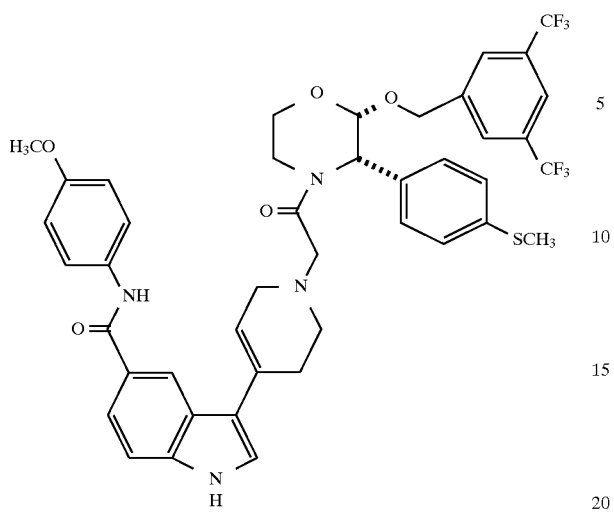

EXAMPLE 27

Preparation of 4-{[4-[5-(methoxy)indol-3-yl]-1,2,3,6-tetrahydropyridin-1-yl]acetyl}-3-(S)-(4-methylphenyl)-2-(R)-[1-[3,5-bis(trifluoromethyl)phenyl]ethoxy]morpholine

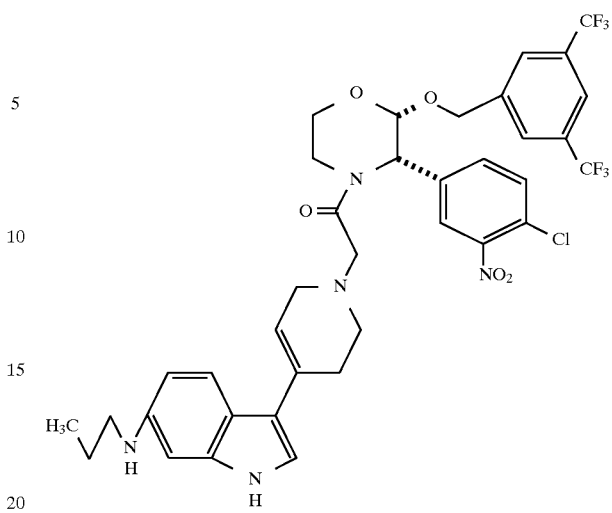

EXAMPLE 28a

Preparation of 4-{[4-[6-(propyl amino)indo-3-yl]-piperidin-1-yl]acetyl}-3-(S)-(3,4-difluorophenyl)-2-(R)-[1-[3,5-bis(trifluoromethyl)phenyl]ethoxy]morpholine

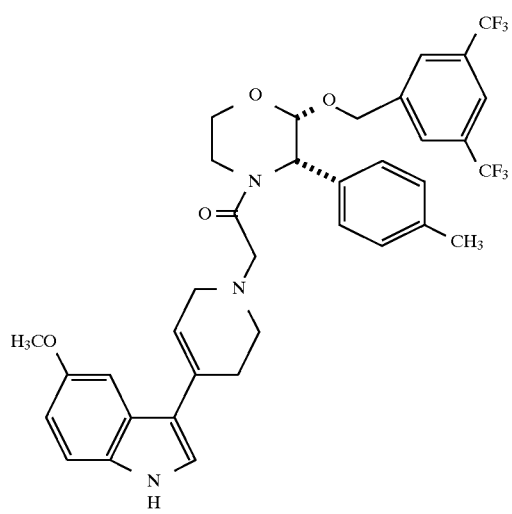

EXAMPLE 28

Preparation of 4-{[4-[6-(propylamino)indol-3-yl]-1,2,3,6-tetrahydropyridin-1-yl]acetyl}-3-(S)-(3-nitro-4-chlorophenyl)-2-(R)-[1-[3,5-bis(trifluoromethyl)phenyl]ethoxy]morpholine

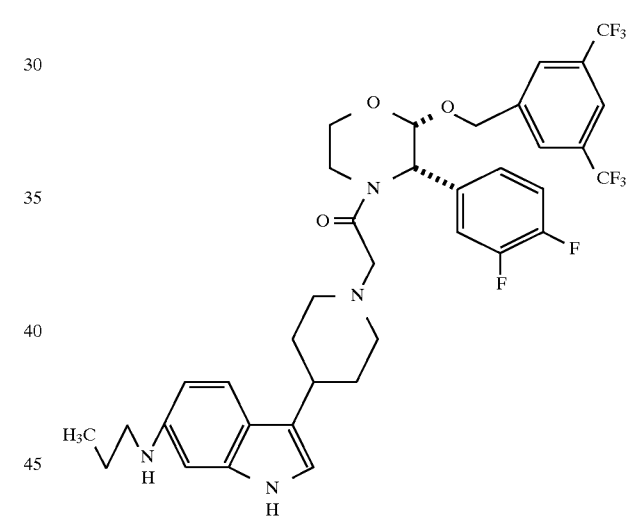

EXAMPLE 29

Preparation of 4-{[4-[6-(acetyl)indol-3-yl]-piperidin-1-yl]acetyl}-3-(S)-(3,4-diethoxyphenyl)-2-(R)-[1-[3,5-bis(trifluoromethyl)phenyl]ethoxy]morpholine

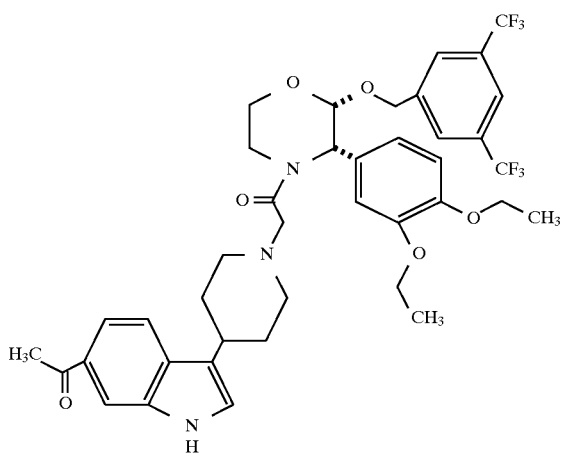

EXAMPLE 30

Preparation of 4-{[4-[5-(acetoxy)indol-3-yl]-piperidin-1-yl]acetyl}-3-(S)-(3,methoxy-4-methylphenyl)-2-(R)-[1-[3,5-bis(trifluoromethyl)phenyl]ethoxy]morpholine

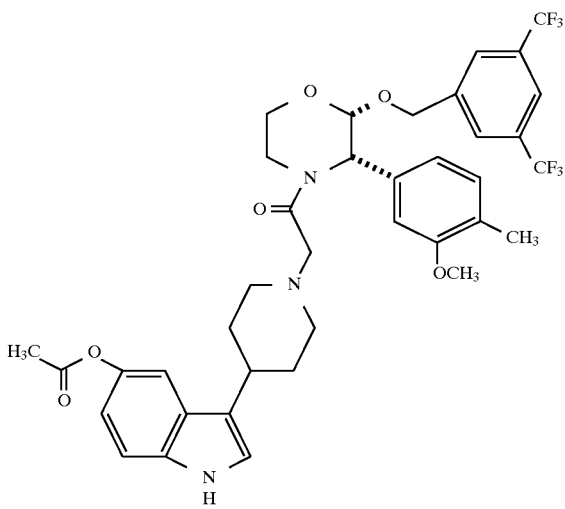

EXAMPLE 31

Preparation of 4-{[4-[5-(phenoxy)indol-3-yl]-pipendin-1-yl]acctyl}-3-(S)-(4-bromophenyl)-2-(R)-[1-[3,5-bis(trifluoromethyl)phenyl]ethoxy]morpholine

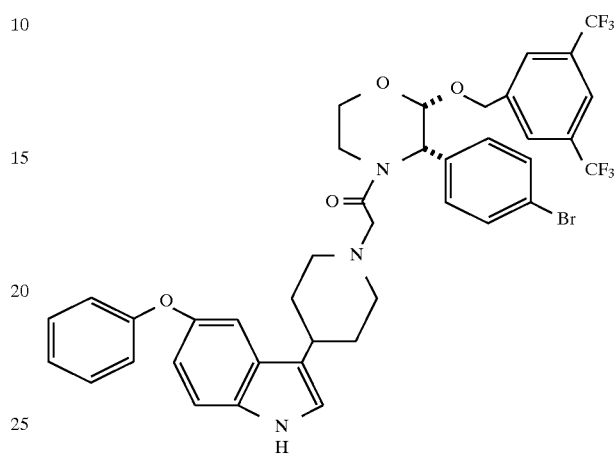

EXAMPLE 32

Preparation of 4-{[4-[5-[(benzylamino)carbonyl]indol-3-yl]-1,2,3,6-tetrahydropyridin-1-yl]acetyl}-3-(S)-(4-methylphenyl)-2(R)-[1-[3,5-bis(methyl)phenyl]ethoxy]morphoine

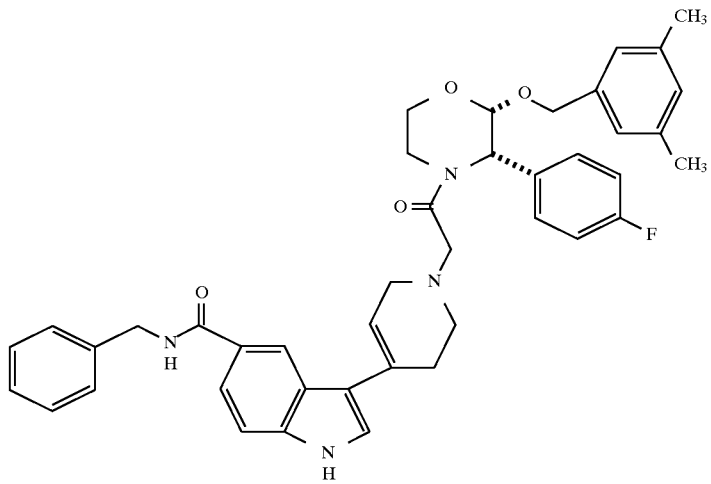

A 10 ml tear drop flask is charged with 4-bromoacetyl-3-(S)-(4-methylphenyl)-2-(R)-[1-[3,5-bis(methyl)phenyl]ethoxy]morpholine (1 eq.), powdered potassium carbonate (4 eq.) and 4-[5-[(benzlyamino)carbonyl]indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of thc reaction is monitored by thin layer chromatography.

The reaction mixture is then poured into water and the solids are collected by vacuum filtration. The solids are dried in a vacuum oven overbight to yield the desired title product.

EXAMPLE 33

Preparation of 4-{([4-[5-(hydroxy)indol-3-yl]-2,3,6-tetrahydropyridin-1-yl]acetyl}-3-(S)-(4-trifluoromethylphenyl)-2-(R)-[1-[4-chorophenyl]ethoxy]morpholine

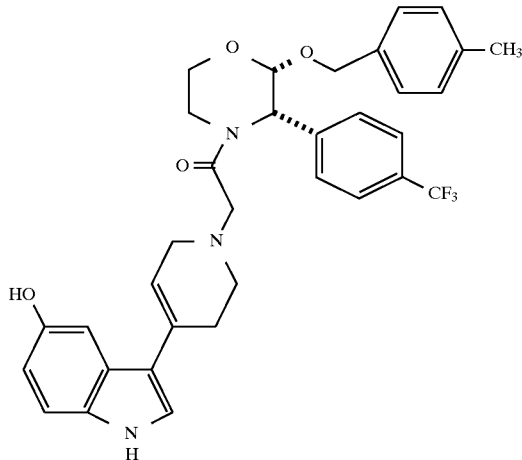

A 10 ml tear drop flask is charged with 4-bromoacetyl-3-(S)-(4-trifluoromethylphenyl)-2-(R)-[1-[4-methylphenyl]ethoxy]morpholine (1 eq.), powdered potassium carbonate (4 eq.) and 4-[5-(hydroxy)indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

EXAMPLE 34

Preparation of 4-{[4-[5-(4-fluorobenzoylamino)indol-3-yl]-1,2,3,6-tetrahydropyridin-1-yl]acetyl}-3-(S)-[4-(prop-2-enyl)phenyl]-2-(R)-[1-[3,4-dichlorophenyl]ethoxy]morpholine

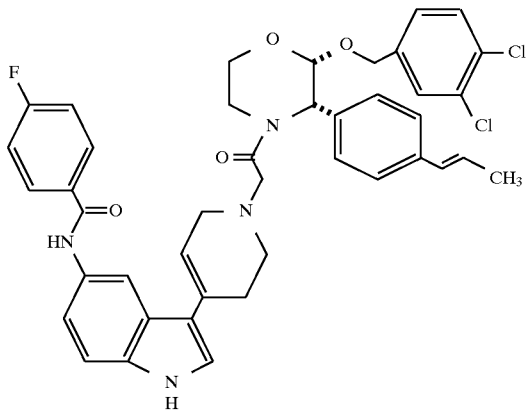

A 10 ml tear drop flask is charged with 4-bromoacetyl-3-(S)-[4-(prop-2-enyl)phenyl]-2-(R)-[1-[3,4-dichlorophenyl]ethoxy]morpholine (1 eq.), powdered potassium carbonate (4 eq.) and 4-[5-(4-fluorobenzoylamino)indol-3-yl]-1,2,3,6-tetrahydropyridine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

EXAMPLE 35

Preparation of 4-{[4-[5-(4-fluorobenzoylamiino)indol-3-yl]-piperidin-1-yl]acetyl}-3-(S)-(4-isopropylphenyl)-2-(R)-[1-[4-acetylphenyl]ethoxy]morpholine

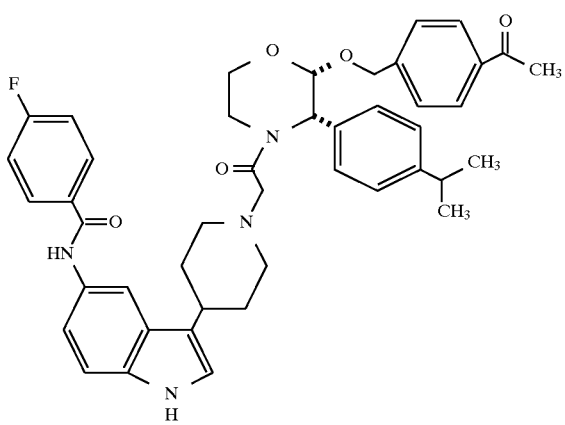

A 10 ml tear drop flask is charged with 4-bromoacetyl-3-(S)-(4-isopropylphenyl)-2-(R)-[1-[4-acetylphenyl]ethoxy]morpholine (1 eq.), powdered potassium carbonate (4 eq.) and 4-[5-(hydroxy)indol-3-yl]-piperidine (1 eq.). To the resulting mixture is added 2.0 ml of N,N-dimethylformamide. The resulting mixture is then placed under a nitrogen atmosphere and permitted to stir overnight. The progress of the reaction is monitored by thin layer chromatography.

The reaction mixture is then poured into water and the solids are collected by vacuum filtration. The solids are dried in a vacuum oven overnight to yield the desired title product.

The following Examples are prepared essentially as described in the above examples, except that other intermediates are employed.

EXAMPLE 36

Preparation of 4-{[4-[5-(4-trifluoromethylbenzoylamino)indol-3-yl]-piperidin-1-yl]acetyl}-3-(S)-(4-propylsulfonylphenyl)-2-(R)-[1-[4-(ethylamino)phenyl]ethoxy]morpholine

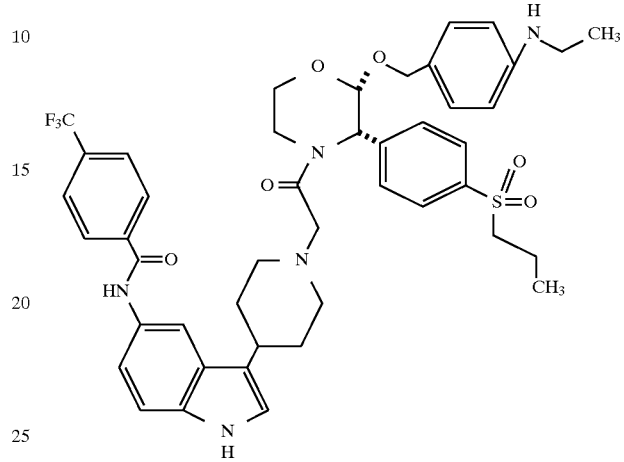

EXAMPLE 37

Preparation of 4-{[4-[5-(4-isopropylbenzoylamino)indol-3-yl]piperidin-1-yl]acetyl}3-(S)-(3,4-dimethoxyphenyl)-2-(R)-[1-[4-(methylsulfonyl)phenyl]ethoxy]morpholine

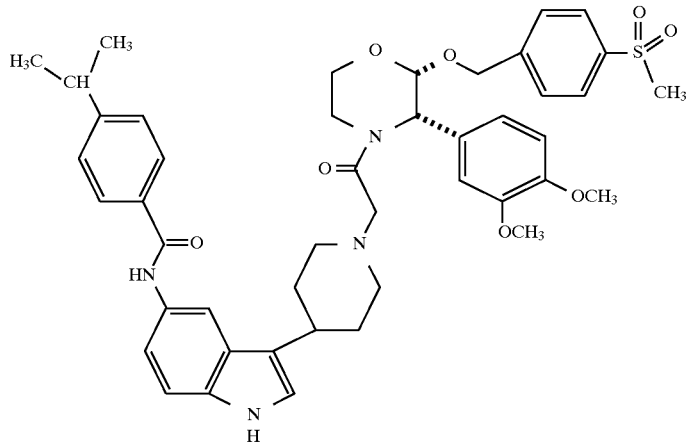

EXAMPLE 38

Preparation of 4-{[4-[5-(4-isopropylbenzoyl)indol-3-yl]-piperidin-1-yl]acetyl}-3-(S)-(3-acetylphenyl)-2-(R)-[1-[3-(prop-2-enyl)phenyl]ethoxy]morpholine

EXAMPLE 39

Preparation of 4-{[4-[5-(4-fluorobenzoyl)indol-3-yl]-piperidin-1-yl]acetyl}-3-(S)-(4-cyanophenyl)-2-(R)-[1-[3,5-bis(ethoxy)phenyl]ethoxy]morpholine

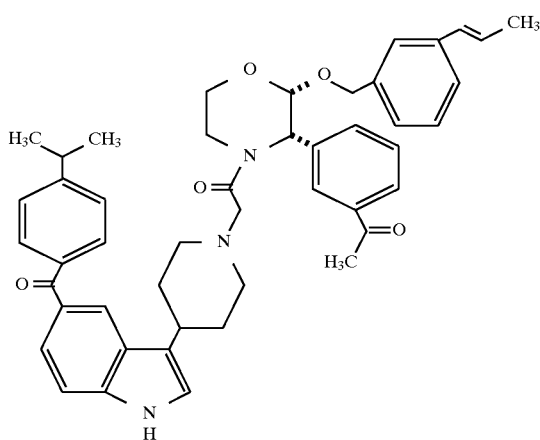

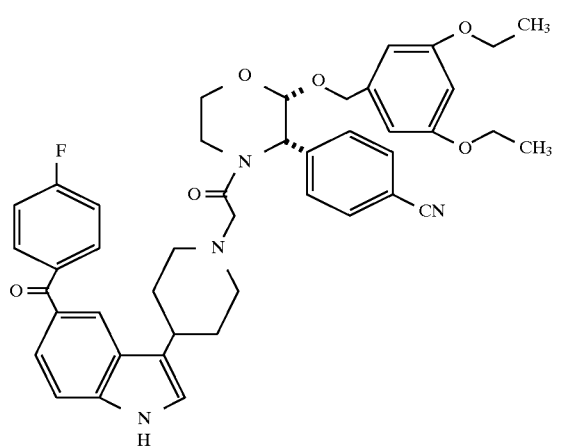

EXAMPLE 40

Preparation of 4-{[4-[5-[[(4-isopropylphenyl)amino]carbonyl]indol-3-yl]-piperidin-1-yl]acetyl}-3-(S)-{4-[(N,N,-dimethylamino)carbonyl]fluorophenyl}-2-(R)-[1-[3-trifluoromethylphenyl]ethoxy]morpholine

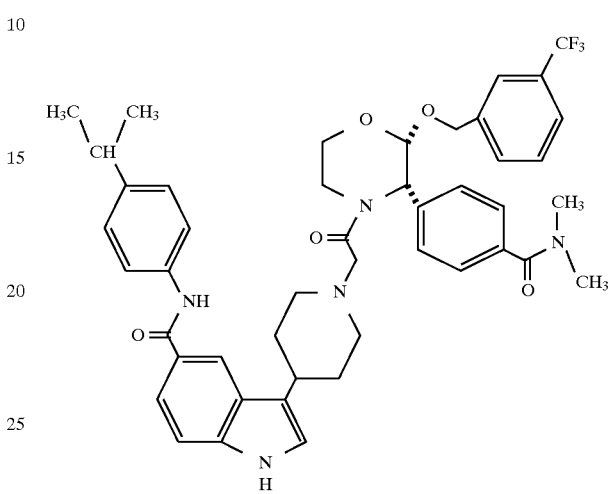

EXAMPLE 41

Preparation of 4-{[4-[5-[[(4-methoxyphenyl)amino]carbonyl]indol-3-yl]-piperidin-1-yl]acetyl}-3-(S)-(3,4-dichlorophenyl)-2-(R)-[-1-[3-(propoxycarbonyl)phenyl]ethoxy]morpholine

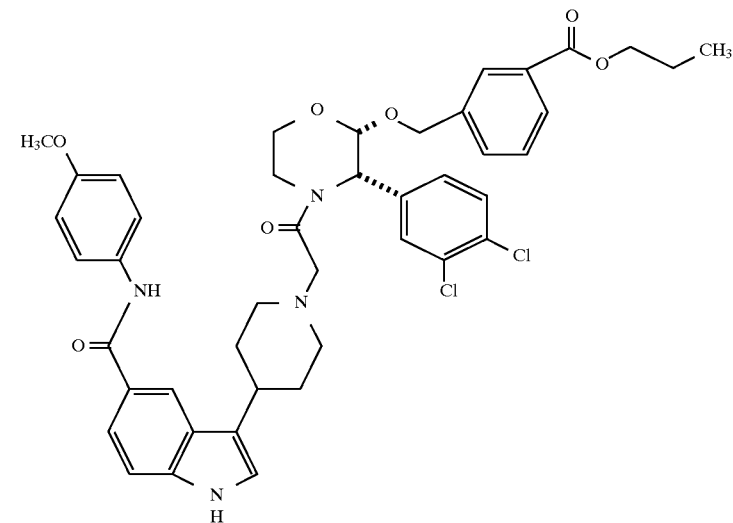

EXAMPLE 42

Preparation of 4-{[4-[5-[[(4-methoxyphenyl)amino]carbonyl]indol-3-yl]-1,2,3,6-tetrahydropyridin-1-yl]acetyl}-3-(S)-(4-methylthiophenyl)-2-(R)-[1-[4-[(N,N-dimethylamino)carbonyl]phenyl]ethoxy]morpholine

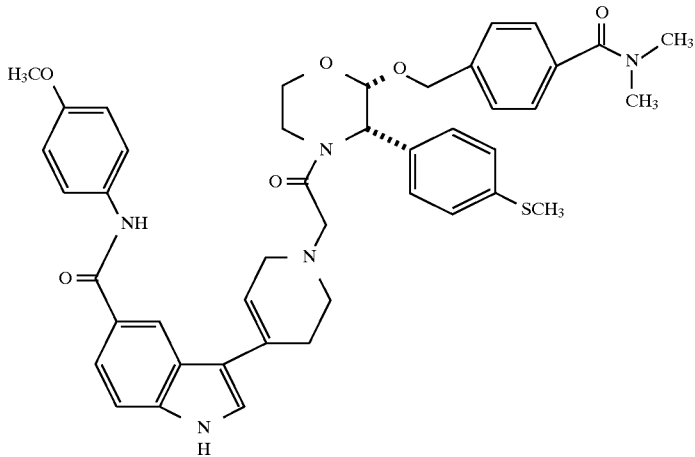

EXAMPLE 43

Preparation of 4-{[4-[5-(methoxy)indol-3-yl]-1,2,3,6-tetrahydropyridin-1-yl]acetyl}-3-(S)-(4-methylphenyl)-2-(R)-[1-[3,4,5-tri(trifluoromethyl)phenyl]ethoxy]morpholine

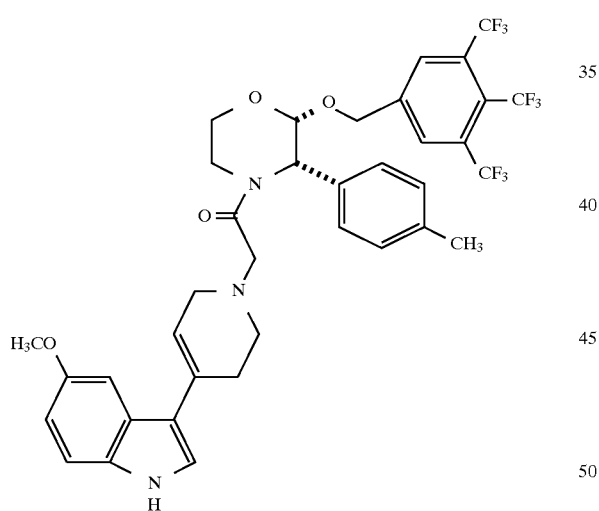

EXAMPLE 44

Preparation of 4-{[4-[6-(propylamino)indol-3-yl]-1,2,3,6-tetrahydropyridin-1-yl]acetyl}-3-(S)-(3-nitro-4-chlorophenyl)-2-(R)-[1-[3,5-bis(trifluoromethyl)phenyl]ethoxy]morpholine

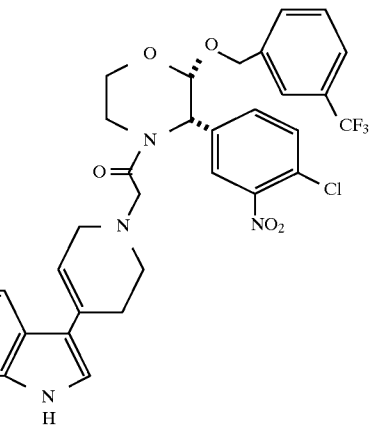

EXAMPLE 45

Preparation of 4-{[4-[6-(propylamino)indol-3-yl]-piperidin-1-yl]acetyl}-3-(S)-(3,4-difluorophenyl)-2-(R)-[1-[3-(prop-2-ynyl)trifluoromethyl)phenyl]ethoxy]morpholine

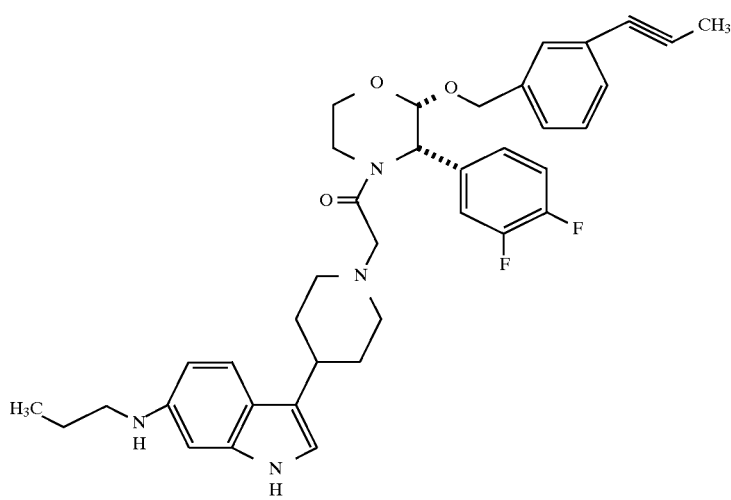

EXAMPLE 46

Preparation of 4-{[4-[6-(acetyl)indol-3-yl]-piperidin-1-yl]acetyl}-3-(S)-(3,4-diethoxyphenyl)-2-(R)-[1-[3-(cyano)phenyl]ethoxy]morpholine

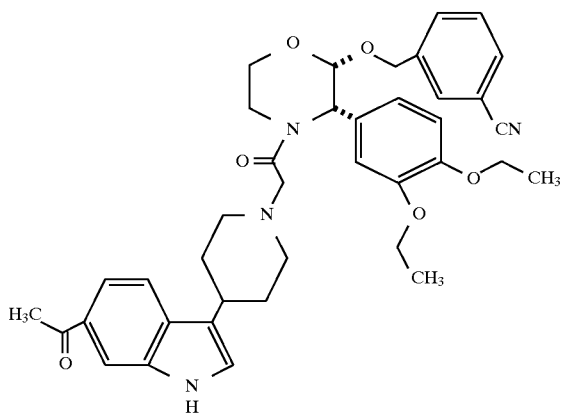

EXAMPLE 47

Preparation of 4-{[4-[5-(acetoxy)indol-3-yl]-piperidin-1-yl]acetyl}-3-(S)-(3,methoxy-4-methylphenyl)-2-(R)-[1-[3-(isopropyl)phenyl]ethoxy]morpholine

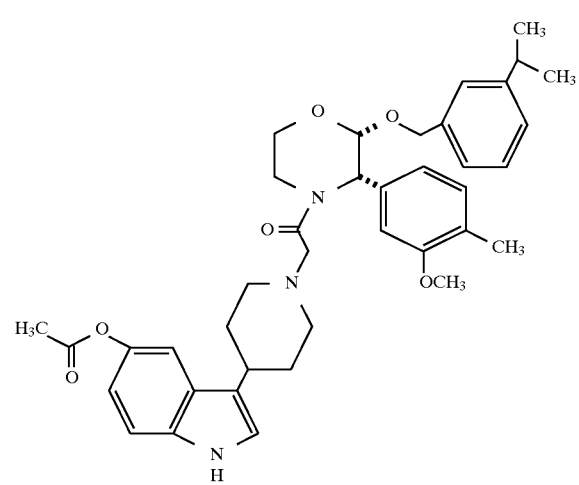

EXAMPLE 48

Preparation of 4-{[4-[5-(phenoxy)indol-3-yl]-piperidin-1-yl]acetyl}-3-(S)-(4-bromophenyl)-2-(R)-[1-[3,5-dibromophenyl]ethoxy]morpholine

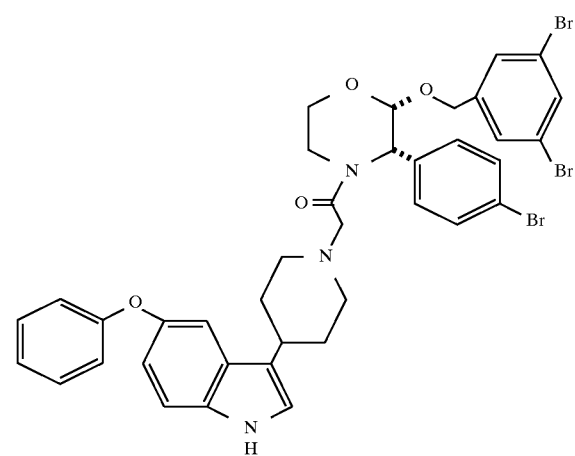

The other compounds of Formula I may be prepared essentially as described above, employing other intermediates. The compounds described above are illustrative of the species encompassed within the present invention.

The compounds of Formula I are useful as tachykinin receptor antagonists. The biological activity of the compounds of the present invention is evaluated employing an initial screening assay which rapidly and accurately measured the binding of the tested compound to known NK-1 and NK-2 receptor sites. Assays useful for evaluating tachykinin receptor antagonists are well known in the art. See. e.g., J. Jukic, et al., *Life Sciences,* 49:1463–1469 (1991); N. Kucharczyk, et al., *Journal of Medicinal Chemistry,* 36:1654–1661 (1993); N. Rouissi, et al., *Biochemical and Biophysical Research Communications,* 176:894–901 (1991).

NK-1 Receptor Binding Assay

Radioreceptor binding assays are performed using a derivative of a previously published protocol. D. G. Payan, et al., *Journal of Immunology,* 133:3260–3265 (1984). In this assay an aliquot of IM9 cells ($1 \times 10^6$ cells/tube in RPMI 1604 medium supplemented with 10% fetal calf serum) is incubated with 20 pM $^{125}$I-labeled substance P in the presence of increasing competitor concentrations for 45 minutes at 4° C.

The IM9 cell line is a well-characterized cell line which is readily available to the public. See. e.g., *Annals of the New York Academy of Science,* 190:221–234 (1972); *Nature (London),* 251:443–444 (1974); *Proceedings of the National Academy of Sciences (USA),* 71:84–88 (1974). These cells are routinely cultured in RPMI 1640 supplemented with 50 μg/ml gentamicin sulfate and 10% fetal calf serum.

The reaction is terminated by filtration through a glass fiber filter harvesting system using filters previously soaked for 20 minutes in 0.1% polyethylenimine. Specific binding of labeled substance P is determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, are grown in 75 cm$^2$ flasks or roller bottles in minimal essential medium (alpha modification) with 10% fetal bovine serum. The gene sequence of the human NK-2 receptor is given in N. P. Gerard, et al., *Journal of Biological Chemistry,* 265:20455–20462 (1990).

For preparation of membranes, 30 confluent roller bottle cultures are dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells are pooled and centrifuged at 1,000 RPM for 10 minutes in a clinical centrifuge. Membranes are prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets are washed once using the above procedure and the final pellets are resuspended in 100–120 ml 50 mM Tris buffer, pH 7.4, and 4 ml aliquots stored frozen at −70° C. The protein concentration of this preparation is 2 mg/ml.

For the receptor binding assay, one 4-ml aliquot of the CHO-hNK-2R membrane preparation is suspended in 40 ml of assay buffer containing 50 mM Tris, pH 7.4, 3 mM manganese chloride, 0.02% bovine serum albumin (BSA) and 4 μg/ml chymostatin. A 200 μl volume of the homogenate (40 μg protein) is used per sample. The radioactive ligand is [$^{125}$I]iodohistidyl-neurokinin A (New England Nuclear, NEX-252), 2200 Ci/mmol. The ligand is prepared in assay buffer at 20 nCi per 100 μl; the final concentration in the assay is 20 pM. Non-specific binding is determined using 1 μM eledoisin. Ten concentrations of eledoisin from 0.1 to 1000 nM are used for a standard concentration-response curve.

All samples and standards are added to the incubation in 10 μl dimethylsulfoxide (DMSO) for screening (single dose) or in 5 μl DMSO for IC$_{50}$ determinations. The order of additions for incubation is 190 or 195 μl assay buffer, 200 μl homogenate, 10 or 5 μl sample in DMSO, 100 μl radioactive ligand. The samples are incubated 1 hour at room temperature and then filtered on a cell harvester through filters which had been presoaked for two hours in 50 mM Tris buffer, pH 7.7, containing 0.5% BSA. The filter is washed 3 times with approximately 3 ml of cold 50 mM Tris buffer, pH 7.7. The filter circles are then punched into 12×75 mm polystyrene tubes and counted in a gamma counter.

As the compounds of Formula I are effective tachykinin receptor antagonists, these compounds are of value in the treatment of a wide variety of clinical conditions which are characterized by the presence of an excess of tachykinin. Thus, the invention provides methods for the treatment or prevention of a physiological disorder associated with an excess of tachykinins, which method comprises administering to a mammal in need of said treatment an effective amount of a compound of Formula I or a pharmaceutically acceptable salt, solvate or prodrug thereof. The term "physiological disorder associated with an excess of tachykinins" encompasses those disorders associated with an inappropriate stimulation of tachykinin receptors, regardless of the actual amount of tachykinin present in the locale.

These physiological disorders may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease, emesis, and irritable bowel syndrome; disorders of bladder function such as bladder detrusor hyper-reflexia and incontinence; atherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Reynaud's disease; and pain or nociception, for example, that attributable to or associated with any of the foregoing conditions, especially the transmission of pain in migraine. For example the compounds of Formula I may suitably be used in the treatment of disorders of the central nervous system such as anxiety, psychosis, and schizophrenia; neurodegenerative disorders such as Alzheimer's disease and Down's syndrome; respiratory diseases such as bronchospasm and asthma; inflammatory diseases such as inflammatory bowel disease, osteoarthritis and rheumatoid arthritis; adverse immunological disorders such as rejection of transplanted tissues; gastrointestinal disorders and diseases such as disorders associated with the neuronal control of viscera such as ulcerative colitis, Crohn's disease, emesis, and irritable bowel syndrome; incontinence; disorders of blood flow caused by vasodilation; and pain or nociception, for example, that attributable to or associated with any of the foregoing conditions or the transmission of pain in migraine.

Many of the compounds of Formula I are selective tachykinin receptor antagonists. These compounds preferentially bind one tachykinin receptor subtype compared to other such receptors. Such compounds are especially preferred.

For example, NK-1 antagonists are most especially preferred in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, angina pain, and genitourinary tract-related pain including cystitis.

In addition to pain, NK-1 antagonists are especially preferred in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; atherosclerosis; inflammatory conditions, such as inflammatory bowel disease, ulcerative colitis, Crohn's disease, rheumatoid arthritis, osteoarthritis, neurogenic inflammation, allergies, rhinitis, cough, dermatitis, urticaria, psoriasis, conjunctivitis, emesis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are especially preferred in the treatment of urinary incontinence, bronchospasm, asthma, adult respiratory distress syndrome, motility disorders of the gastrointestinal tract, such as irritable bowel syndrome, and pain.

In addition to the above indications the compounds of Formula I are particularly useful in the treatment of emesis, including acute, delayed, or anticipatory emesis, such as emesis induced by chemotherapy, radiation, toxins, pregnancy, vestibular disorders, motion, surgery, migraine, and variations in intercranial pressure. Most especially, the compounds of Formula I are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates, and other compounds with an alkylating action, such as nitrosoureas, cisplatin, and dacarbazine; antimetabolites, for example, folic acid, purine, or pyrimidine antagonists; mitotic inhibitors, for example vinca alkaloids and derivatives of podophyllotoxin; and cytotoxic antibiotics.

Particular examples of chemotherapeutic agents are described, for instance, by D. J. Stewart in NAUSEA AND VOMITING: RECENT RESEARCH AND CLINICAL ADVANCES, (J. Kucharczyk, et al., eds., 1991), at pages 177–203. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin, daunorubicin, procarbazine, mitomycin, cytarabine, etoposide, methotrexate, 5-fluorouracil, vinblastine, vincristine, bleomycin, and chlorambucil. R. J. Gralla, et al., *Cancer Treatment Reports*, 68:163–172 (1984).

The compounds of Formula I are also of use in the treatment of emesis induced by radiation, including radiation therapy such as in the treatment of cancer, or radiation sickness; and in the treatment of post-operaive nausea and vomiting.

It will be appreciated that a compound of Formula I may be presented together with another therapeutic agent as a combined preparation for simultaneous, separate, or sequential use for the relief of emesis. Such combined preparations may be, for example, in the form of a twin pack.

As one example, it may be desirable to employ a compound of Formula I in conjunction with a bronchodilator (such as a $\beta_2$-adrenergic receptor antagonist) for the treatment of asthma. The present invention also provides, therefore, a composition comprising a compound of Formula I, a bronchodilator, and a pharmaceutically acceptable carrier.

Recent reports have demonstrated that the co-administration of an NK-1 antagonist and an NK-2 antagonist has a synergistic advantage over either alone. United Kingdom Patent Application GB 2,274,777 A, published Aug. 10, 1994. This line of reasoning would suggest, therefore, that a compound of Formula I which has antagonist activity at both the NK-1 and NK-2 receptors, even though neither such activity is optimal when compared to the other compounds of Formula I, may be preferable to a compound having optimal activity at one or the other receptor.

The compounds of the present invention also have activity as serotonin agonists. The biological efficacy of a compound believed to be effective as a serotonin agonist may be confirmed by first employing an initial screening assay which rapidly and accurately measures the binding of the test compound to one or more serotonin receptors. Once the binding of the test compound to one or more serotonin receptors is established, the in vivo activity of the test compound on the receptor is established. Assays useful for evaluating serotonin agonists are well known in the art. See. e.g., E. Zifa and G. Fillion, infra; D. Hoyer, et al., infra, and the references cited therein.

Many serotonin binding receptors have been identified. These receptors are generally grouped into seven classes on the basis of their structure and the pharmacology of the receptor as determined by the binding efficiency and drug-related characteristics of numerous serotonin receptor-binding compounds. In some of the groups several subtypes have been identified. [For a relatively recent review of 5-hydroxytryptamine receptors, see, E. Zifa and G. Fillion, *Pharamcological Reviews*, 44:401–458 (1992); D. Hoyer, et al., *Pharamcological Reviews*, 46:157–203 (1994).] Table I, infra, lists the seven classes of serotonin receptors as well as several known subtypes. This table also provides the physiological distribution of these receptors as well as biological responses mediated by the receptor class or subtype, if any such response is known. This table is derived from D. Hoyer, et al, "VII. International Union of Pharmacology Classification of Receptors for 5-Hydroxytryptamine (Serotonin)", *Pharmacological Reviews*, 46:157–203 (1994), a publication of the Serotonin Club Receptor Nomenclature Committee of the IUPHAR Committee for Receptor Nomenclature.

The Hoyer, et al., reference describes for each class or subtype one or more compounds which have efficacy as antagonists or agonists for the receptor.

The 5-$HT_1$ family includes subtypes which can be grouped together based on the absence of introns in the cloned genes, a common G-coupled protein transduction system (inhibition of adenylate cyclase), and similar operational characteristics. The 5-$HT_1$ family of inhibitory receptors includes subtypes A, B, D, E, and F. The 5-$HT_1$ G protein-linked receptors general inhibit the production of cyclic adenosine monophosphate (cAMP), while the 5-$HT_2$ G protein linked receptors stimulate phosphoinosytol hydrolysis.

The 5-$HT_{1A}$ receptor was the first cloned human serotonin receptor. Activated 5-$HT_{1A}$ receptors expressed in HeLa cells inhibit forskolin-stimulated adenylate cyclase activity. The 5-$HT_{1D}$ receptor was originally identified in bovine brain membrane by Heuring and Peroutka. R. E. Heuring and S. J. Peroutka, *Journal of Neuroscience*, 7:894–903 (1987). The 5-$HT_{1D}$ receptors are the most common 5-HT receptor subtype in the human brain and may be identical to the 5-$HT_1$-like receptor in the cranial vasculature. S. D. Silberstein, *Headache*, 34:408–417 (1994). Sumatriptan and the ergot alkaloids have high affinity for both the human 5-$HT_{1D}$ and the 5-$HT_{1B}$ receptors. Id.

The 5-$HT_{1F}$ subtype of receptor has low afity for 5-carboxamidotryptamine (5-CT) unlike the other 5-HT receptors, except for the 5-$HT_{1E}$ subtype. Unlike the 5-$HT_{1E}$ receptors, however, the 5-$HT_{1F}$ receptors do show affinity for sumatriptan. Compounds modulating the 5-$HT_{1F}$ receptor are especially preferred for the treatment of migraine. European Patent Publication 705,600, published Apr. 10, 1996.

TABLE I

| Receptor Type | Subtype | Location | Response |
|---|---|---|---|
| 5-$HT_1$ | 5-$HT_{1A}$ | Neuronal, mainly in CNS | Neuronal hyperpolarisation, hypotension |
| | 5-$HT_{1B}$ | CNS and some peripheral nerves | Inhibition of neurotransmitter release |
| | 5-$HT_{1D}$ | Mainly CNS | Inhibition of neurotransmitter release |
| | 5-$HT_{1E}$ | Only CNS | Inhibition of adenylyl cyclase |
| | 5-$HT_{1F}$ | Mainly CNS | Inhibition of adenylyl |

TABLE I-continued

| Receptor Type | Subtype | Location | Response |
|---|---|---|---|
| | | | cyclase |
| | 5-$HT_1$-like | Intracranial vasculature | Smooth muscle contraction |
| 5-$HT_2$ | 5-$HT_{2A}$ | Vascular smooth muscle, platelets, lung, CNS, gastrointestinal tract | Vasoconstriction, platelet aggregation, bronchoconstriction |
| | 5-$HT_{2B}$ | Mainly peripheral, some CNS | Rat stomach fundie muscle contraction |
| | 5-$HT_{2C}$ | CNS (high density in choroid plexus) | upregulates phosphoinositide turnover |
| 5-$HT_3$ | | Peripheral and central neurones | Depolarization |
| 5-$HT_4$ | | Gastrointestinal tract, CNS, heart, urinary bladder | Activation of acetylcholine release in gut, tachycardia, upregulates cAMP in CNS neurones |
| 5-$HT_5$ | 5-$HT_{5A}$ | CNS | Not known |
| | 5-$HT_{5D}$ | CNS | Not known |
| 5-$HT_6$ | | CNS | Activation of adenylyl cyclase |
| 5-$HT_7$ | | CNS | Activation of adenylyl cyclase |

Serotonin Receptor Binding Activity

Binding to the 5-$HT_{1F}$ receptor

The ability of a compound to bind to a serotonin receptor was measured using standard procedures. For example, the ability of a compound to bind to the 5-$HT_{1F}$ receptor subtype was performed essentially as described in N. Adham, et al., *Proceedings of the National Academy of Sciences (USA)*, 90:408–412 (1993).

The cloned 5-$HT_{1F}$ receptor was expressed in stably transfected LM(tk–) cells. Membrane preparations were made by growing these transfected cell lines to confluency. The cells were washed twice with phosphate-buffered saline, scraped into 5 ml of ice-cold phosphate-buffered saline, and centrifuged at 200×g for about five minutes at 4° C. The pellet was resuspended in 2.5 ml of cold Tris buffer (20 mM Tris.HCl, pH 7.4 at 23° C., 5 mM EDTA) and homogenized. The lysate was centrifuged at 200×g for about five minutes at 4° C. to pellet large fragments. The supernatant was then centrifuged at 40,000×g for about 20 minutes at 4° C. The membranes were washed once in the homogenization buffer and resuspended in 25 mM glycylglycine buffer, pH 7.6 at 23° C.

Radioligand binding studies were performed using [$^3$H] 5-HT (20–30 Ci/mmol). Competition experiments were done by using various concentrations of drug and 4.5–5.5 nM [$^3$H]5-HT. Nonspecific binding was defined by 10 $\mu$M 5-HT. Binding data were analyzed by nonlinear-regression analysis. $IC_{50}$ values were converted to $K_i$ values using the Cheng-Prusoff equation.

For comparison purposes, the binding affinities of compounds for various serotonin receptors may be determined essentially as described above except that different cloned receptors are employed in place of the 5-$HT_{1F}$ receptor clone employed therein.

Serotonin Agonist Activity

Adenylate Cyclase Activity.

Adenylate cyclase activity was determined in initial experiments in LM(tk–) cells, using standard techniques. See. e.g., N. Adham, et al., supra,; R. L. Weinshank, et al.,

*Proceedings of the National Academy of Sciences (USA),* 89:3630–3634 (1992), and the references cited therein.

Intracellular levels of cAMP were measured using the clonally derived cell line described above. Cells were pre-incubated for about 20 minutes at 37° C. in 5% carbon dioxide, in Dulbecco's modified Eagle's medium containing 10 mM HEPES, 5 mM theophylline, and 10 μM pargyline. Varying concentrations of the test compounds were added to the medium to determine inhibition of forskolin-stimulated adenylate cyclase.

Animal and human clinical models demonstrating the effectiveness of the methods of the present invention are well known to those skilled in the art. For example, the following experiment clearly demonstrates the inhibitory effect of the compounds of the present invention on an animal model predictive of migraine therapies.

Neurogenic Plasma Estravasation in the Dural Layer Induced by Electrical Stimulation Harlan Sprague-Dawley rats (225–325 g) or guinea pigs from Charles River Laboratories (225–325 g) were anesthetized with sodium phenobarbitol (65 mg/kg or 45 mg/kg, respectively, intraperitoneally) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally for rats; 4 mm posteriorly and 3.2 and 5.2 mm laterally for guinea pigs—all coordinates reference to bregma). Pairs of stainless steel stimulating electrodes, insulated except for the tips, were lowered through the holes in both hemispheres to a depth of 9 mm (rats) or 10.5 mm (guinea pigs) from dura.

The femoral vein was exposed and a dose of the test compound was injected intravenously (1 ml/kg). Approximately seven minutes later, a 50 mg/kg dose of Evans Blue, a fluorescent dye, was also injected intravenously. The Evans Blue complexed with proteins in the blood and functioned as a marker for protein extravasation. Exactly ten minutes post-injection of the test compound, the left trigeminal ganglion was stimulated for three minutes at a current intensity of 1.0 mA (5 Hz, 4 msec duration) with a potentiostat/galvanostat.

Fifteen minutes following the stimulation, the animals were killed and exanguinated with 20 ml of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope equipped with a grating monochromator and a spectrophotometer was used to quantify the amount of Evans Blue dye in each tissue sample. An excitation wavelength of approximately 535 nm was utilized and the emission intensity at 600 nm was determined. The microscope was equipped with a motorized stage and was interfaced with a personal computer. This facilitated the computer-controlled movement of the stage with fluorescence measurements at 25 points (500 μm steps) on each dural sample. The mean and standard deviation of the measurements were determined by the computer.

The dural extravasation induced by electrical stimulation of the trigeminal ganglion was an ipsilateral effect (i.e. it occurs only on the side of the dura in which the trigeminal ganglion was stimulated). This allowed the other, unstimulated, half of the dura to be used as a control. The ratio of the amount of extravasation in the dura from the stimulated side compared to the unstimulated side was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was estimated.

Numerous recent publications have demonstrated that migraine and numerous psychiatric disorders are co-morbid. Individuals with migraine are at a higher risk of developing these disorders, which are described in detail infra. N. Breslau, et al., *Headache,* 34:387–393 (1994); K. R. Merikangas, et al., *Archives of General Psychiatry,* 47:849–853 (1990); N. Breslau, et al., *Psychiatry Research,* 37:11–23 (1991); W. F. Stewart, et al., *Psychosom. Medicine,* 51:559–569; J. Jarman, et al., *Journal of Neurological and Neurosurgical Psychiatry,* 53:573–575 (1990); V. Glover, et al., *Journal of Psychiatric Research,* 27:223–231 (1993); N. Breslau and G.C. Davis, *Journal of Psychiatric Research,* 27:211–221 (1993); and K. R. Merikangas, et al., *Journal of Psychiatric Research,* 27:197–210 (1993). This invention describes the co-morbidity of migraine pain and other pains such as those exemplified herein.

The methods of the present invention are particularly advantageous in the treatment or prevention of pain. These methods are especially preferred in the treatment or prevention of types of pain generally considered refractory to standard non-sedating, non-addictive therapies. Such pains include chronic pain, such as neuropathic pain, and post-operative pain, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, angina pain, and genitourinary tract-related pain including cystitis.

Animal and human clinical models demonstrating the effectiveness of the compounds of the present invention in treating psychiatric disorders are well known to those skilled in the art. For example, in evaluating the methods of the present invention in treating or preventing anxiety the following models may be employed.

Punished Responding

The antianxiety activity of the compositions employed in the method of the present invention is established by demonstrating that these compositions increase punished responding. This procedure has been used to establish antianxiety activity in clinically established compositions.

According to this procedure, the responding of rats or pigeons is maintained by a multiple schedule of food presentation. In one component of the schedule, responding produces food pellet presentation only. In a second component, responding produces both food pellet presentation and is also punished by presentation of a brief electric shock. Each component of the multiple schedule is approximately 4 minutes in duration, and the shock duration is approximately 0.3 seconds. The shock intensity is adjusted for each individual animal so that the rate of punished responding is approximately 15 to 30% of the rate in the unpunished component of the multiple schedule. Sessions are conducted each weekday and are approximately 60 minutes in duration. Vehicle or a dose of composition are administered 30 minutes to 6 hours before the start of the test session by the subcutaneous or oral route. Composition effects for each dose for each animal are calculated as a percent of the vehicle control data for that animal. The data are expressed as the mean the standard error of the mean.

Monkey Taming Model

The antianxiety activity of the compositions is established by demonstrating that the compositions are effective in the monkey taming model. Plotnikoff, *Res. Comm. Chem. Path. & Pharmacol.*, 5:128–134 (1973) describes the response of rhesus monkeys to pole prodding as a method of evaluating the antiaggressive activity of a test composition. In this method, the antiaggressive activity of a composition is considered to be indicative of its antianxiety activity. Hypoactivity and ataxia are considered to be indicative of a sedative component of the composition. The present study is designed to measure the pole prod response-inhibition induced by a composition of this invention in comparison with that of a standard antianxiety composition employing a compound such as diazepam as a measure of antiaggressive potential, and to obtain an indication of the duration of action of the compound.

Male and female rhesus or cynomologous monkeys, selected for their aggressiveness toward a pole, are housed individually in a primate colony room. Compositions or appropriate vehicle are administered orally or subcutaneously and the animals are observed by a trained observer at varying times after drug administration. A minimum of three days (usually a week or more) elapses between treatments. Treatments are assigned in random fashion except that no monkey receives the same composition two times consecutively.

Aggressiveness and motor impairment are graded by response to a pole being introduced into the cage as described in Table II. The individuals responsible for grading the responses are unaware of the dose levels received by the monkeys.

TABLE II

Grading of Monkey Response to Pole Introduction

| Response | Grade | Description |
|---|---|---|
| Attack | 2 | Monkey immediately grabbed and/or bit pole as it was placed at opening in cage. |
|  | 1 | Monkey grabbed and/or bit pole only after the tip was extended into the cage 12 inches or more. |
|  | 0 | No grabbing or biting observed. |
| Pole Push | 2 | Monkey grabbed the pole to attack it or push it away. |
|  | 1 | Monkey touched the pole only in attempting to avoid it or rode on the pole (avoidance). |
|  | 0 | No pushing, grabbing or riding of the pole observed. |
| Biting | 2 | Monkey bit aggressively and frequently. |
|  | 1 | Monkey bit weakly or infrequently |
|  | 0 | No biting observed. |
| Ataxia | 2 | Monkey exhibited a marked loss of coordination. |
|  | 1 | Slight loss of coordination observed. |
|  | 0 | No effects on coordination observed. |
| Hypoactivity | 2 | Marked: Monkey was observed in a prone position. May or may not have responded by rising and moving away when experimenter approached. |

TABLE II-continued

|  | 1 | Slight: Monkey did not retreat as readily when experimenter approached |
|  | 0 | None. |
| Antiagression Activity of Drug Dose |
|  | + | Dose of drug was active in decreasing global assessment of aggressive behavior |
|  | − | Dose of drug was not active in decreasing aggressive behavior |

Human Clinical Trials

Finally, the antianxiety activity of the named compositions and methdods can be demonstrated by human clinical trials. The study is designed as a double-blind, parallel, placebo-controlled multicenter trial. The patients are randomized into four groups, placebo and 25, 50, and 75 mg tid of test composition. The dosages are administered orally with food. Patients are observed at four visits to provide baseline measurements. Visits 5–33 served as the treatment phase for the study.

During the visits, patients and their caregivers were questioned and observed for signs of agitation, mood swings, vocal outbursts, suspiciousness, and fearfulness. Each of these behaviors are indicative of the effect of the test composition on an anxiety disorder.

The patient to be benefited by practice of the present invention is a patient having one or more of the disorders discussed in detail below, or who is at a heightened risk of contracting such disorder. Diagnosis of these disorders, or the identification of a patient at risk of one or more of them, is to be made by a physician or psychiatrist. It is presently believed that the combination of serotonin receptor agonists and tachykinin receptor antagonists results in the alleviation of the effects of the disorder from which the patient suffers, or even the elimination of the disorder completely.

A patient with a heightened risk of contracting one of the present disorders is a patient, in the present contemplation, who is more likely than is a normal person to fall victim to that disorder. The patient may have suffered from the disorder in the past, and be at risk of a relapse, or may exhibit symptoms which demonstrate to the physician or psychiatrist that the patient is under an abnormal risk of developing the disorder in its full form.

The disorders which are treated or prevented in the practice of the present invention may be described as follows.

bulimia nervosa obsessive-compulsive disorder premenstrual dysphoric disorder substance abuse substance dependence panic disorder panic attack agoraphobia post-traumatic stress disorder dementia of Alzheimer's type social phobia attention deficit hyperactivity disorder disruptive behavior disorder intermittent explosive disorder borderline personality disorder chronic fatigue syndrome premature ejaculation depression and behavioral problems associated with head injury, mental retardation or stroke.

Most of the disorders discussed here are described and categorized in the DIAGNOSTIC AND STATISTICAL MANUAL OF MENTAL DISORDERS, (4th edition, 1994), published by the American Psychiatric Association (hereinafter referred to as DSM). In the discussion below, the DSM codes for the disorders will be given where appropriate.

Bulimia nervosa, DSM 307.51, is characterized by uncontrollable binge eating, followed by self-induced purging, usually vomiting. Its prevalence is as high as 1%–3% among adolescent and young adult females. The disorder is well characterized and recognized by the health professions. The essential features of it are binge eating and inappropriate compensatory methods to prevent weight gain. Further, individuals with the disorder are excessively influenced by body shape and weight.

Obsessive-compulsive disorder, DSM 300.3, is characterized by recurrent obsessions or compulsions which are severe enough to be time consuming or cause distress or impairment of the patient's life. Obsessions are persistent ideas, thoughts, impulses or images which are recognized by the patient to be intrusive and inappropriate and cause anxiety or distress. The individual senses that the obsession is alien, not under control and not the kind of thought that the patient would expect to have. Common obsessions include repeated thoughts about contamination, repeated doubts, a need to arrange things in a particular order, aggressive or horrific impulses and sexual imagery. Compulsions are repetitive behaviors, such as hand washing, or mental acts, such as counting or repeating words silently, the goal of which is to prevent or reduce anxiety or distress. By definition, compulsions are either clearly excessive or not realistically connected with that which they are designed to neutralize or prevent. Obsessive-compulsive disorder is rather common, with an estimated lifetime prevalence of 2.5%.

Substance abuse and substance dependence, very well known in most societies at present, come about when the patient becomes addicted or habituated to the improper use of a drug or other substance. Several different varieties of substance abuse and dependence will be discussed in detail below. It will be understood that substance abuse or dependence often results in additional disorders, including intoxication, withdrawal symptoms, delirium, psychotic disorders, hallucinations, mood disorders, anxiety disorders, sexual dysfunctions, or sleep disorders. Recognized substance abuse and substance dependence disorders which are part of the present invention include the following:

amphetamine dependence, DSM 304.40 amphetamine abuse, DSM 305.70 cannabis dependence, DSM 304.30 cannabis abuse, DSM 305.20 cocaine dependence, DSM 304.20 cocaine abuse, DSM 305.60 hallucinogen dependence, DSM 304.50 hallucinogen abuse, DSM 305.30 inhalant dependence, DSM 304.60 inhalant abuse, DSM 305.90 nicotine dependence, DSM 305.10 opioid dependence, DSM 304.00 opioid abuse, DSM 305.50 phencyclidine dependence, DSM 304.90 phencyclidine abuse, DSM 305.90 sedative, hypnotic or anxiolytic dependence, DSM 304.10 sedative, hypnotic or anxiolytic abuse, DSM 305.40 polysubstance dependence, DSM 304.80

The prevalence and deleterious effects of substance dependence and substance abuse are almost too well known to discuss. The disorders are characterized, in general, by a compulsion to use the substance in question in order to obtain its effects, regardless of the ill-effects of the substance or the difficulty, expense or danger of obtaining it. Some substances of abuse, such as cannabis and cocaine, have run through entire sections of society and have damaged or ruined untold numbers of lives. The importance of the ability to relieve such disorders in accordance with the present invention is obviously of great significance.

Panic attack, panic disorder and agoraphobia, categorized as DSM 300.01, 300.21 and 300.22, affect between 1.5% and 3.5% of the population. The disorders are characterized by irrational sense of imminent danger or doom, an urge to escape, or a fear of being in a situation from which escape might be difficult. The patient exhibits symptoms such as palpitations, accelerated heart rate, sweating, sensations of shortness of breath, chest pain, nausea, dizziness, fear of dying, and the like, and may have such attacks very frequently.

Social phobia, DSM 300.23, produces a marked and persistent fear of social or performance situations in which embarrassment may occur. Exposure to such a situation may result in a panic attack, or other anxious response. Most often, patients with the disorder simply avoid situations of the type which they dread, producing an obvious dislocation in the patient's life. The prevalence of social phobia has been reported as from 3% to 13%, on a lifetime basis.

Post-traumatic stress disorder, DSM 309.81, afflicts patients following exposure to a traumatic stress involving personal experience of an event involving actual or threatened death of injury. Such traumatic events include experiences such as military combat, personal assault, kidnapping, terrorist attack, torture, natural or man-made disasters, severe accidents, or being diagnosed with a dreaded illness. Learning about such events occurring to others, particularly a family member or close friend, also may produce the disorder. Triggering events which symbolize the traumatic event, such as an anniversary, may recreate the stress and bring on the disorder long after the event is passed. Patients strive to avoid stimuli associated with the trauma, even to the point of amnesia or reduced responsiveness to other people in general. Prevalence of post-traumatic stress disorder has been reported at from 1% to as much as 14%, and has been reported at 50% and more in studies of individuals who are at risk of the disorder.

Dementia of the Alzheimer's type, DSM 290.11, 290.12, 290.13, 290.10, 290.3, 290.20, 290.21 and 290.0, affects between 2% and 4% of the population over 65 years old. The prevalence increases with age, particularly after 75 years of age, and is associated with Alzheimer's disease. In most patients, brain atrophy or deterioration is present, and is associated with the dementia.

Attention deficit hyperactivity disorder, DSM 314.01 and 314.00, is primarily recognized as a disorder of children, but may well be found in adults as well. It is characterized by symptoms such as lack of attention, impulsivity, and excessive activity, resulting in high expenditure of effort accompanied with a low degree of accomplishment. Patients have difficulty or find it impossible to give attention to details, cannot sustain attention in tasks or even play, and make careless mistakes. They fail to listen to or follow through on instructions, lose things, and are easily distracted by extraneous events. The difficulty of such patients in carrying out useful lives is obvious from the mere recital of the symptoms.

Disruptive behavior disorder, DSM 312.9, is a condition characterized by aggressive, destructive, deceitful and defiant activity.

Intermittent explosive disorder, DSM 312.34, is characterized by episodes of failure to resist aggressive impulses, resulting in assault or destruction of property. The degree of aggressiveness expressed during episodes of this disorder is grossly disproportionate to any provocation or triggering stress. The Southeastern Asian condition of amok is an episode of this disorder, cases of which have been reported in Canada and the United States as well.

Borderline personality disorder, DSM 301.83, is marked by a pervasive pattern of instability of interpersonal relationships and self-image, and marked impulsivity which begins by early adulthood. Patients have a pattern of unstable and intense relationships, very quickly developing a very close relationship and then quickly devaluing the other person. Patients may gamble, spend irresponsibly, binge eat, abuse substances, engage in unsafe sex or drive recklessly. Patients often display recurrent suicidal behavior or self-injurious behavior. The prevalence is estimated to be about 2% of the population.

Premature ejaculation, DSM 302.75, is characterized by the inability of a male to delay orgasm as long as is desired.

Depression and behavioral problems associated with head injury, mental retardation or stroke are treated in the exercise of the present invention. Such depression and behavioral problems are distinct from the usual such disorders, because of their origin. Depression, of course, of the general type is quite prevalent and is now well-known, being well treated with pharmaceuticals such as, for example, fluoxetine.

Chronic fatigue syndrome is a condition which has been variously described and diagnosed. It is sometimes categorized as a low-grade viral infection, particularly caused by the Epstein-Barr virus. Since that virus is very widely found in the population, however, the diagnosis is problematic. An alternative characterization of chronic fatigue syndrome is a physical-psychological disorder of the depression type, characterized primarily by lack of energy and listlessness.

Premenstrual dysphoric disorder is characterized by symptoms such as feelings of sadness, hopelessness or self-deprecation; anxiety or tenseness; tearfulness and lability of mood; persistent irritability and anger; decreased interest in usual activities or withdrawal from relationships; difficulty concentrating and the like. It is not classified formally by DSM but is discussed in detail there. The pattern of symptoms occurs in most cycles, frequently beginning the week prior to menses. Frequently, the disorder markedly interferes with the patient's life in all respects during the attack of the disorder. The prevalence of the disorder in its most profound form has been estimated at 3%–5%, but there has been little systematic study on the course and stability of the condition.

Animal and human clinical models demonstrating the effectiveness of the compounds of the present invention in treating the common cold or allergic rhinitis are well known to those skilled in the art. For example, in evaluating the methods of the present invention in treating or ameliorating the symptoms of the common cold or allergic rhinitis, it is especially preferred to ultimately employ clinical studies. Human clinical studies for evaluating the effectiveness of a treatment of either of these disorders are described in U.S. Pat. Nos. 5,240,694, issued Aug. 31, 1993, and 5,252,602, issued Oct. 12, 1993, the entirety of which are herein incorporated by reference.

The compounds of Formula I have demonstrated efficacy as both tachykinin receptor antagonists and as serotonin agonists. As noted supra, U.S. patent application Ser. No. 08/318,391, filed Oct. 5, 1994, describes a synergistic effect on the combination of a serotonin agonist and a tachykinin receptor antagonist in treating migraine. U.S. patent application Ser. No. 08/387,056, filed Feb. 10, 1995, describes a synergistic effect on the combination of a serotonin agonist and a tachykinin receptor antagonist in treating a variety of psychiatric disorders. U.S. patent application Ser. No. 08/408,238, filed Mar. 22, 1995, describes a synergistic effect on the combination of a serotonin agonist and a tachykinin receptor antagonist in treating a variety of types of pain and nociception. U.S. patent application Ser. No. 60/000074, filed Jun. 8, 1995, describes a synergistic effect on the combination of a serotonin agonist and a tachykinin receptor antagonist in treating the common cold or allergic rhinitis.

The compounds of the present invention are, therefore, especially preferred for the treatment of these disorders. The most preferred methods of treatment of the present invention are those methods for which a synergistic effect can be demonstrated for compositions having activity as both tachykinin receptor antagonists and serotonin agonists.

The advantages of any synergistic combination therapy are obvious. Among its other advantages, this combination therapy greatly increases the therapeutic index of a composition in treating these nociceptive disorders. A markedly decreased amount of a serotonin agonist may now be administered to a patient, presumably greatly lessening the likelihood and severity of any adverse events. The reduced amount of active ingredient necessary for a therapeutic effect makes possible other routes of formulation than those currently employed.

Rapid onset formulations such as buccal or sublingual may now be developed. Sustained release formulations are now more feasible due to the lower amounts of active ingredient necessary.

While it is possible to administer a compound employed in the methods of this invention directly without any formulation, the compounds are usually administered in the form of pharmaceutical compositions comprising a pharmaceutically acceptable excipient and at least one active ingredient. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 15 mg of medicament, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 ml |

FORMULATION EXAMPLE 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or buccal tablets, each containing 10 mg of active ingredient, may be prepared as follows:

| Ingredient | Quantity Per Tablet |
|---|---|
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued April 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method for the treatment or prevention of a physiological disorder associated with an excess of tachykinins, which method comprises administering to a mammal in need of said treatment an effective amount of a compound of the formula

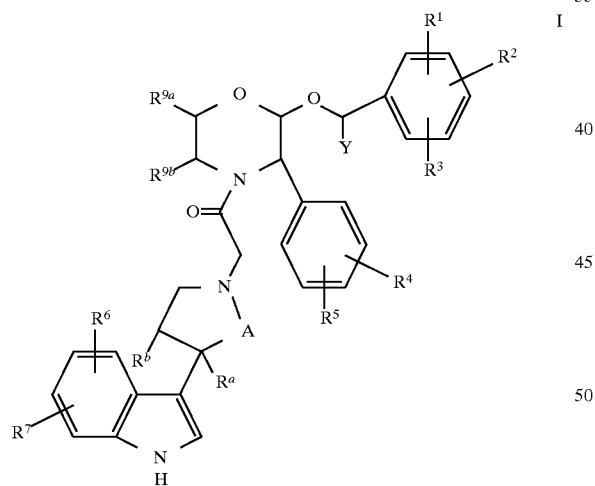

wherein:
- $R^1$ is hydrogen, halo, $C_1$–$C_6$ alkyl, $C_1$–$C_6$ alkoxy, trifluoromethyl, nitro, cyano, thiol, $C_1$–$C_6$ alkylthio, $C_1$–$C_6$ alkylsulfinyl, $C_1$–$C_6$ alkylsulfonyl, $C_2$–$C_6$ alkoxycarbonyl, $C_2$–$C_6$ carbamoyl, —C(O)-di($C_1$–$C_6$ alkyl)amino, $C_2$–$C_6$ alkenyl, $C_2$–$C_6$ alkynyl, $C_2$–$C_6$ alkanoyl, or $C_1$–$C_6$ alkoxy optionally substituted with $C_1$–$C_6$ alkoxy;
- $R^2$ is hydrogen, halo, $C_1$–$C_6$ alkyl, $C_1$–$C_6$ alkoxy optionally substituted with $C_1$–$C_6$ alkoxy, or trifluoromethyl;
- $R^3$ is hydrogen, halo, or trifluoromethyl;
- $R^4$ is hydrogen, halo, trifluoromethyl, $C_1$–$C_6$ alkyl, $C_1$–$C_6$ alkoxy, nitro, cyano, thiol, $C_1$–$C_6$ alkylthio, $C_1$–$C_6$ alkylsulfinyl, $C_1$–$C_6$ alkylsulfonyl, $C_2$–$C_6$ alkoxycarbonyl, $C_2$–$C_6$ carbamoyl, —C(O)-di($C_1$–$C_6$ alkyl)amino, $C_2$–$C_6$ alkenyl, $C_2$–$C_6$ alkynyl, $C_2$–$C_6$ alkanoyl, or $C_1$–$C_6$ alkoxy optionally substituted with $C_1$–$C_6$ alkoxy;
- $R^5$ is hydrogen, halo, $C_1$–$C_6$ alkoxy optionally substituted with $C_1$–$C_6$ alkoxy, or trifluoromethyl;
- $R^{9a}$ and $R^{9b}$ are each independently hydrogen, or $C_1$–$C_6$ alkyl, or are joined so to form, together with the carbon atoms to which they are attached, a $C_3$–$C_8$ cycloalkyl ring;
- Y is hydrogen or $C_1$–$C_6$ alkyl, said $C_1$–$C_6$ alkyl group being optionally substituted with one or two hydroxy groups;
- A is —CH2—, —CH$_2$CH$_2$—, or —CH$_2$CH$_2$CH$_2$—;
- $R^a$ is hydrogen or hydroxy, and $R^b$ is hydrogen, or $R^a$ and $R^b$ are taken together to form a bond;
- $R^6$ and $R^7$ are independently taken from the group consisting of halo, trifluoromethyl, hydrogen, $C_1$–C6 alkoxy, $C_1$—$C_6$ alkyl, $C_1$—$C_6$ alkylthio, $C_1$—$C_6$ alkylamino, hydroxy, cyano, $C_2$–$C_7$ alkanoyl, $C_2$–$C_7$ alkanoyloxy, benzamido, phenoxy, carboxamido, hydroxy, benzyloxy, phenyl($C_2$–$C_7$ alkanoyl)—, $C_1$–$C_6$ phenyl($C_2$–$C_7$ carbamoyl)—,
  said benzamido, phenoxy, benzyloxy, phenyl($C_2$–$C_7$ alkanoyl)—, and phenyl($C_2$–$C_7$ carbamoyl)— being optionally substituted with one or more groups selected from the group consisting of halo, trifluoromethyl, $C_1$–$C_6$ alkyl, $C_1$–$C_6$ alkoxy, cyano, hydroxy, amino and nitro;

or a pharmaceutically acceptable salt, solvate, or prodrug thereof.

2. A compound of the formula

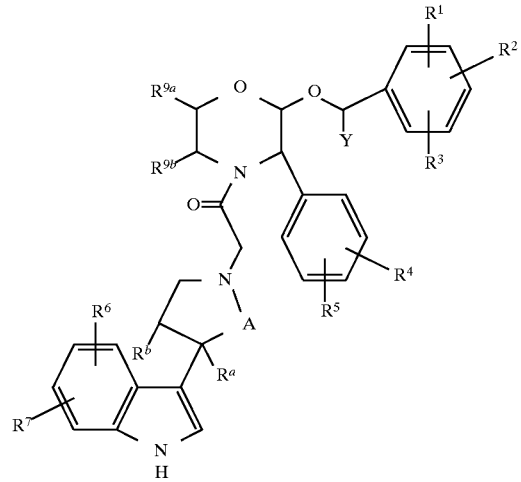

wherein:
- $R^1$ is hydrogen, halo, $C_1$–$C_6$ alkyl, $C_1$–$C_6$ alkoxy, trifluoromethyl, nitro, cyano, thiol, $C_1$–$C_6$ alkylthio, $C_1$–$C_6$ alkylsulfinyl, $C_1$–$C_6$ alkylsulfonyl, $C_2$–$C_6$ alkoxycarbonyl, $C_2$–$C_6$ carbamoyl, —C(O)-di($C_1$–$C_6$ alkyl)amino, $C_2$–$C_6$ alkenyl, $C_2$–$C_6$ alkynyl, $C_2$–$C_6$ alkanoyl, or $C_1$–$C_6$ alkoxy optionally substituted with $C_1$–$C_6$ alkoxy;
- $R^2$ is hydrogen, halo, $C_1$–$C_6$ alkyl, $C_1$–$C_6$ alkoxy optionally substituted with $C_1$–$C_6$ alkoxy, or trifluoromethyl;
- $R^3$ is hydrogen, halo, or trifluoromethyl;
- $R^4$ is hydrogen, halo, trifluoromethyl, $C_1$–$C_6$ alkyl, $C_1$–$C_6$ alkoxy, nitro, cyano, thiol, $C_1$–$C_6$ alkylthio, $C_1$–$C_6$ alkylsulfinyl, $C_1$–$C_6$ alkylsulfonyl, $C_2$–$C_6$ alkoxycarbonyl, $C_2$–$C_6$ carbamoyl, —C(O)-di($C_1$–$C_6$ alkyl)amino, $C_2$–$C_6$ alkenyl, $C_2$–$C_6$ alkynyl, $C_2$–$C_6$ alkanoyl, or $C_1$–$C_6$ alkoxy optionally substituted with $C_1$–$C_6$ alkoxy;

$R^5$ is hydrogen, halo, $C_1$–$C_6$ alkoxy optionally substituted with $C_1$–$C_6$ alkoxy, or trifluoromethyl;

$R^{9a}$ and $R^{9b}$ are each independently hydrogen, or $C_1$–$C_6$ alkyl, or are joined so to form, together with the carbon atoms to which they are attached, a $C_3$–$C_8$ cycloalkyl ring;

Y is hydrogen or $C_1$–$C_6$ alkyl, said $C_1$–$C_6$ alkyl group being optionally substituted with one or two hydroxy groups;

A is —$CH_2$—, —$CH_2CH_2$—, or —$CH_2CH_2CH_2$—;

$R^a$ is hydrogen or hydroxy, and $R^b$ is hydrogen, or $R^a$ and $R^b$ are taken together to form a bond;

$R^6$ and $R^7$ are independently taken from the group consisting of halo, trifluoromethyl, hydrogen, $C_1$–$C_6$ alkoxy, $C_1$–$C_6$ alkyl, $C_1$–$C_6$ alkylthio, $C_1$–$C_6$ alkylamino, hydroxy, cyano, $C_2$–$C_7$ alkanoyl, $C_2$–$C_7$ alkanoyloxy, benzamido, phenoxy, carboxamido, hydroxy, benzyloxy, phenyl($C_2$–$C_7$ alkanoyl)—, $C_1$–$C_6$ phenyl($C_2$–$C_7$ carbamoyl)—, said benzamido, phenoxy, benzyloxy, phenyl($C_2$–$C_7$ alkanoyl)—, and phenyl($C_2$–$C_7$ carbamoyl)— being optionally substituted with one or more groups selected from the group consisting of halo, trifluoromethyl, $C_1$–$C_6$ alkyl, $C_1$–$C_6$ alkoxy, cyano, hydroxy, amino and nitro;

or a salt, solvate, or prodrug thereof.

3. A pharmaceutical formulation comprising a compound of the formula

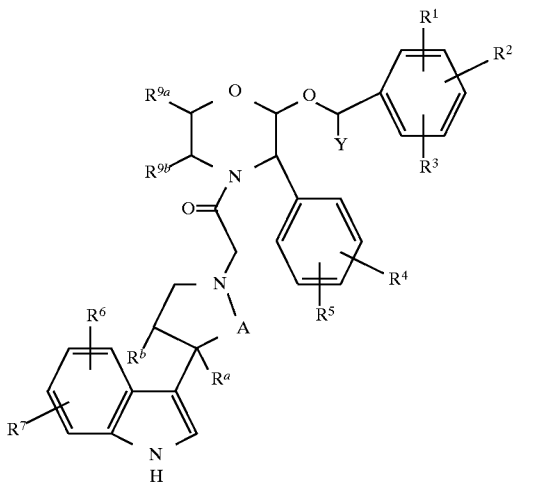

wherein:

$R^1$ is hydrogen, halo, $C_1$–$C_6$ alkyl, $C_1$–$C_6$ alkoxy, trifluoromethyl, nitro, cyano, thiol, $C_1$–$C_6$ alkylthio, $C_1$–$C_6$ alkylsulfinyl, $C_1$–$C_6$ alkylsulfonyl, $C_2$–$C_6$ alkoxycarbonyl, $C_2$–$C_6$ carbamoyl, —C(O)-di($C_1$–$C_6$ alkyl)amino, $C_2$–$C_6$ alkenyl, $C_2$–$C_6$ alkynyl, $C_2$–$C_6$ alkanoyl, or $C_1$–$C_6$ alkoxy optionally substituted with $C_1$–$C_6$ alkoxy;

$R^2$ is hydrogen, halo, $C_1$–$C_6$ alkyl, $C_1$–$C_6$ alkoxy optionally substituted with $C_1$–$C_6$ alkoxy, or trifluoromethyl;

$R^3$ is hydrogen, halo, or trifluoromethyl;

$R^4$ is hydrogen, halo, trifluoromethyl, $C_1$–$C_6$ alkyl, $C_1$–$C_6$ alkoxy, nitro, cyano, thiol, $C_1$–$C_6$ alkylthio, $C_1$–$C_6$ alkylsulfinyl, $C_1$–$C_6$ alkylsulfonyl, $C_2$–$C_6$ alkoxycarbonyl, $C_2$–$C_6$ carbamoyl, —C(O)-di($C_1$–$C_6$ alkyl)amino, $C_2$–$C_6$ alkenyl, $C_2$–$C_6$ alkynyl, $C_2$–$C_6$ alkanoyl, or $C_1$–$C_6$ alkoxy optionally substituted with $C_1$–$C_6$ alkoxy;

$R^5$ is hydrogen, halo, $C_1$–$C_6$ alkoxy optionally substituted with $C_1$–$C_6$ alkoxy, or trifluoromethyl;

$R^{9a}$ and $R^{9b}$ are each independently hydrogen, or $C_1$–$C_6$ alkyl, or are joined so to form, together with the carbon atoms to which they are attached, a $C_3$–$C_8$ cycloalkyl ring;

Y is hydrogen or $C_1$–$C_6$ alkyl, said $C_1$–$C_6$ alkyl group being optionally substituted with one or two hydroxy groups;

A is —$CH_2$—, —$CH_2CH_2$—, or —$CH_2CH_2CH_2$—;

$R^a$ is hydrogen or hydroxy, and $R^b$ is hydrogen, or $R^a$ and $R^b$ are taken together to form a bond;

$R^6$ and $R^7$ are independently taken from the group consisting of halo, trifluoromethyl, hydrogen, $C_1$–$C_6$ alkoxy, $C_1$–$C_6$ alkyl, $C_1$–$C_6$ alkylthio, $C_1$–$C_6$ alkylamino, hydroxy, cyano, $C_2$–$C_7$ alkanoyl, $C_2$–$C_7$ alkanoyloxy, benzamido, phenoxy, carboxamido, hydroxy, benzyloxy, phenyl($C_2$–C7 alkanoyl)—, $C_1$–$C_6$ phenyl($C_2$–C7 carbamoyl)—, said benzamido, phenoxy, benzyloxy, phenyl($C_2$–$C_7$ alkanoyl)—, and phenyl($C_2$–$C_7$ carbamoyl)— being optionally substituted with one or more groups selected from the group consisting of halo, trifluoromethyl, $C_1$–$C_6$ alkyl, $C_1$–$C_6$ alkoxy, cyano, hydroxy, amino and nitro;

or a pharmaceutically acceptable salt, solvate, or prodrug thereof, in combination with one or more pharmaceutically acceptable carriers, diluents, or excipients therefor.

* * * * *